United States Patent
Song et al.

(10) Patent No.: US 10,077,299 B2
(45) Date of Patent: Sep. 18, 2018

(54) METHOD FOR REFINING PROTEIN INCLUDING SELF-CUTTING CASSETTE AND USE THEREOF

(71) Applicant: AbTLAS CO., LTD., Gangwon-do (KR)

(72) Inventors: Byeong Doo Song, Gangwon-do (KR); Jee Sun Yun, Gangwon-do (KR); Hyo Jung Choi, Gangwon-do (KR); Hye In Kim, Gangwon-do (KR); Eung-Suk Lee, Gwangwon-do (KR)

(73) Assignee: AbTLAS CO., LTD. (KR)

( * ) Notice: Subject to any disclaimer, the term of this patent is extended or adjusted under 35 U.S.C. 154(b) by 144 days.

(21) Appl. No.: 14/785,881

(22) PCT Filed: Apr. 25, 2014

(86) PCT No.: PCT/KR2014/003639
§ 371 (c)(1),
(2) Date: Oct. 21, 2015

(87) PCT Pub. No.: WO2014/175690
PCT Pub. Date: Oct. 30, 2014

(65) Prior Publication Data
US 2016/0137720 A1     May 19, 2016

(30) Foreign Application Priority Data
Apr. 25, 2013 (KR) .................. 10-2013-0046322

(51) Int. Cl.
| | |
|---|---|
| *C07K 16/00* | (2006.01) |
| *C12N 15/10* | (2006.01) |
| *C12N 9/52* | (2006.01) |
| *C12N 9/50* | (2006.01) |
| *C07K 1/22* | (2006.01) |

(52) U.S. Cl.
CPC ............... *C07K 16/00* (2013.01); *C12N 9/50* (2013.01); *C12N 9/52* (2013.01); *C12N 15/1093* (2013.01); *C07K 1/22* (2013.01); *C07K 2319/00* (2013.01); *C07K 2319/21* (2013.01); *C07K 2319/30* (2013.01); *C07K 2319/41* (2013.01); *C07K 2319/42* (2013.01); *C07K 2319/50* (2013.01); *C12Y 304/2207* (2013.01)

(58) Field of Classification Search
None
See application file for complete search history.

(56) References Cited

U.S. PATENT DOCUMENTS

| | | | |
|---|---|---|---|
| 2007/0148166 A1* | 6/2007 | Wu .................. | C07K 14/195 424/133.1 |
| 2009/0088372 A1 | 4/2009 | Prasad et al. | |
| 2011/0321183 A1 | 12/2011 | Ploegh et al. | |
| 2016/0025740 A1 | 1/2016 | Song et al. | |
| 2016/0136298 A1 | 5/2016 | Grawunder et al. | |

FOREIGN PATENT DOCUMENTS

| | | |
|---|---|---|
| JP | 2009-55837 A | 3/2009 |
| WO | 2005051976 A2 | 6/2005 |
| WO | 2011056911 A2 | 5/2011 |
| WO | 2013003555 A1 | 1/2013 |
| WO | 2014145441 A1 | 9/2014 |

OTHER PUBLICATIONS

Antos, J., et al., "Lipid Modification of Proteins through Sortase-Catalyzed Transpeptidation", "J Am Chem Soc.", Dec. 3, 2008, pp. 16338-16343, vol. 130, No. 48.
Antos, J., et al., "Site-Specific N—and C-Terminal Labeling of a Single Polypeptide Using Sortases of Different Specificity", "J. AM. CHEM. SOC.", Jul. 17, 2009, pp. 10800-10801, vol. 131, No. 31.
Ilangovan, U., et al., "Structure of sortase, the transpeptidase that anchors proteins to the cell wall of *Staphylococcus aureus*", "PNAS", May 22, 2001, pp. 6056-6061, vol. 98, No. 11.
Kobashigawa, Y., et al., "Attachment of an NMR-invisible solubility enhancement tag using a sortase-mediated protein ligation method", "J Biomol NMR", Jan. 13, 2009, pp. 145-150, vol. 43.
Mao, H., "A self-cleavable sortase fusion for one-step purification of free recombinant proteins", "Protein Expression and Purification", 2004, pp. 253-263, vol. 37.
Ilangovan, U., et al., "Chain A, Structure of Sortase", "NCBI Protein Database Accession No. 1IJA_A", May 22, 2001, pp. 1-2.
Proft, T., "Sortase-mediated protein ligation: an emerging biotechnology tool for protein modification and immobilisation", "Biotechnol Lett", Sep. 1, 2009, pp. 1-10, vol. 32.
Bromberg, Y., et al., "Correlating protein function and stability through the analysis of single amino acid substitutions", "BMC Bioinformatics", Aug. 27, 2009, pp. doi: 10.1186/1471-2105-10-S8-S8, vol. 10, No. 8.
Pakula, A. A., et al., "Genetic Analysis of Protein Stability and Function", "Annual Review of Genetics", 1989, pp. 289-310, vol. 23.

(Continued)

*Primary Examiner* — Suzanne Marie Noakes
(74) *Attorney, Agent, or Firm* — Jones Day

(57) ABSTRACT

The present invention relates to a self-cleaving fusion protein including a target protein, a peptide consisting of amino acid sequence represented by LPXTG, a domain of Sortase A having cleaving function, and a tag, which are sequentially positioned from the amino terminal; a nucleic acid encoding the same; an expression vector including the nucleic acid of the present invention; and a cell transformed with the expression vector of the present invention. In addition, the present invention relates to a method for refining a target protein including culturing, dissolving, and purifying the transformed cell, and a method for preparing a therapeutic antibody-drug conjugate by using the purifying method.

30 Claims, 9 Drawing Sheets
Specification includes a Sequence Listing.

(56) References Cited

OTHER PUBLICATIONS

Madej, M., et al., "Engineering of an Anti-Epidermal Growth Factor Receptor Antibody to Single Chain Format and Labeling by Sortase A-Mediated Protein Ligation", "Biotechnology and Bioengineering", Dec. 26, 2011, pp. 1461-1470, vol. 109, No. 6.

Chen, X., et al., "Fusion Protein Linkers: Property, Design and Functionality", "Advanced Drug Delivery Reviews", Oct. 15, 2013, pp. 1357-1369, vol. 65, No. 10.

Levary, D., et al., "Protein-Protein Fusion Catalyzed by Sortase A", "PLoS ONE", Apr. 6, 2011, pp. e18342, vol. 6, No. 4.

Li, Y., "Self-Cleaving Fusion Tags for Recombinant Protein Production", "Biotechnology Letters", Jan. 26, 2011, pp. 869-881, vol. 33, No. 5.

Popp, M., et al., "Making and Breaking Peptide Bonds: Protein Engineering Using Sortase", "Angewandte Chemie International Edition", 2011, pp. 5024-5032, vol. 50, No. 22.

Swee, L.K., et al., "Sortase-Mediated Modification of DEC205 Affords Optimization of Antigen Presentation and Immunization Against a Set of Viral Epitopes", "Proceedings of the National Academy of Sciences", Jan. 22, 2013, pp. 1428-1433, vol. 110, No. 4.

* cited by examiner

FIG. 1
I. 
II. 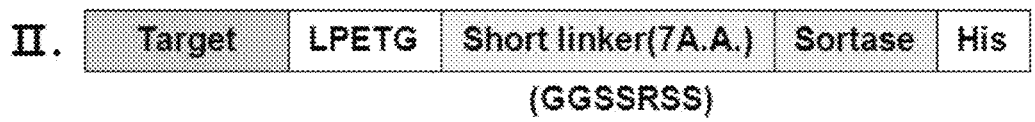
(GGSSRSS)
III. 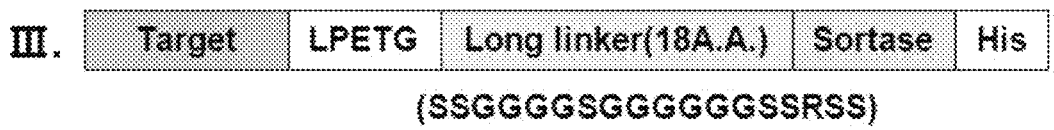
(SSGGGGSGGGGGGSSRSS)
IV. 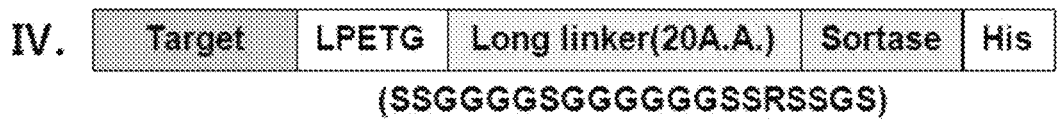
(SSGGGGSGGGGGGSSRSSGS)
FIG. 2
I. 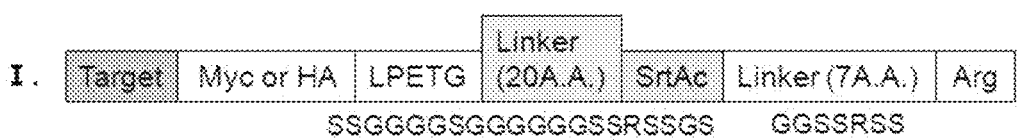
SSGGGGSGGGGGGSSRSSGS    GGSSRSS
II. 
(H4)2L: LEA(EAAAK)₄ALEA(EAAAK)₄ALE

FIG. 3

I. | Target | HA | LPETG | Linker (20A.A.) | SrtAc | C.H.Linker(32A.A.) | His |
SSGGGGSGGGGGGSSRSSGS II. | Target | HA | LPETG | Linker (20A.A.) | SrtAc | A.H.Linker(45A.A.) | His |
SSGGGGSGGGGGGSSRSSGS

FIG. 4

I. | Target | Myc or HA | LPETG | Linker (7A.A.) | SrtAc | No-Linker | 9*Arg / 6*His |
GGSSRSS II. | Target | Myc or HA | LPETG | Linker (18A.A.) | SrtAc | No-Linker | 9*Arg / 6*His |
SSGGGGSGGGGGGSSRSS III. | Target | Myc or HA | LPETG | Linker (20A.A.) | SrtAc | No-Linker | 9*Arg / 6*His / 9*His |
SSGGGGSGGGGGGSSRSSGS IV. | Target | Myc or HA | LPETG | Linker (20A.A.) | SrtAc | Linker (7A.A.) | 9*Arg |
SSGGGGSGGGGGGSSRSSGS          GGSSRSS FIG. 11
A  CaCl2
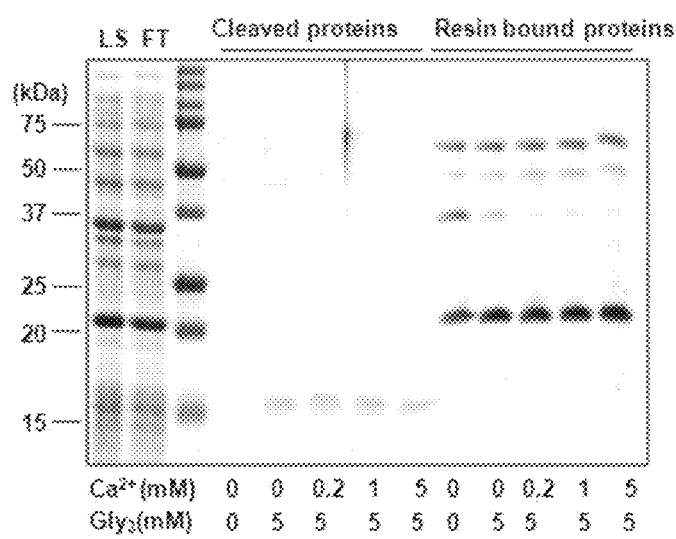
B  Gly-Gly-Gly
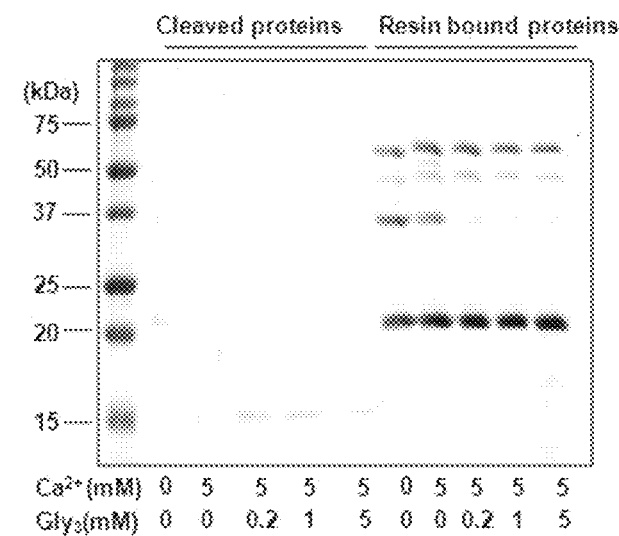

FIG. 16
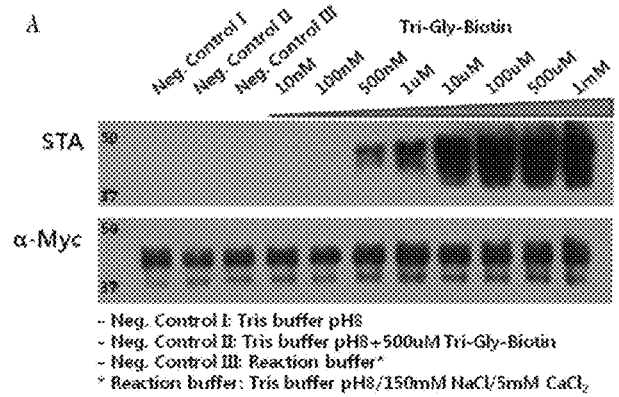
- Neg. Control I: Tris buffer pH8
- Neg. Control II: Tris buffer pH8+500uM Tri-Gly-Biotin
- Neg. Control III: Reaction buffer*
* Reaction buffer: Tris buffer pH8/150mM NaCl/5mM CaCl$_2$
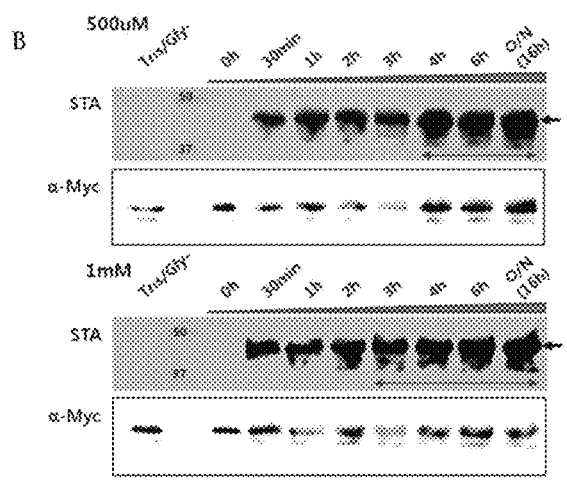
FIG. 17
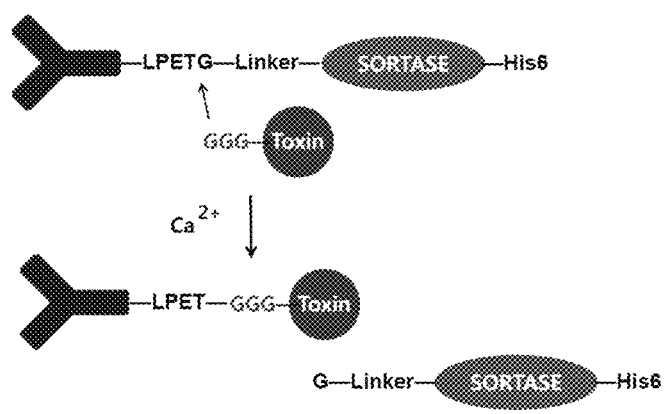

METHOD FOR REFINING PROTEIN INCLUDING SELF-CUTTING CASSETTE AND USE THEREOF

CROSS-REFERENCE TO RELATED APPLICATIONS

This application is a U.S. national phase under the provisions of 35 U.S.C. § 371 of International Patent Application No. PCT/KR14/03639 filed Apr. 25, 2014, which in turn claims priority of Korean Patent Application No. 10-2013-0046322 filed Apr. 25, 2013. The disclosures of such international patent application and Korean priority patent application are hereby incorporated herein by reference in their respective entireties, for all purposes.

TECHNICAL FIELD

The present invention relates to a self-cleaving fusion protein including a target protein, a peptide consisting of amino acid sequence represented by LPXTG, a domain of Sortase A having cleaving function, and a tag, which are sequentially positioned from the amino terminal; a nucleic acid encoding the same; an expression vector including the nucleic acid of the present invention; and a cell transformed with the expression vector of the present invention. In addition, the present invention relates to a method for refining a target protein including culturing, dissolving, and purifying the transformed cell, and a method for preparing a therapeutic antibody-drug conjugate by using the purifying method.

BACKGROUND ART

In accordance with recent development of genetic engineering and biology, there are many attempts to produce or obtain a large amount of specific protein to be used for treatment of various types of industries and diseases. Accordingly, protein combination technology, mass-production technology, and purification technology, and the like, for obtaining a desired protein have been intensively developed.

Frequently, the target protein to be required by human may be produced by culturing a cell transformed with a vector expressing the target protein so that the target protein is expressed. Occasionally, the protein may be expressed in eukaryotic cells, prokaryotic cells, and the like, and in specific cases, the protein may be expressed in transformed plants or transformed animals. For example, a method of expressing a protein in transformed animals that secrets milk to obtain the target protein through the milk of the transformed animals, and the like, has been attempted. In this case, the target protein may be isolated and refined through cell culture or milk.

In a case of expressing a protein in animals and plants or microorganisms which methods for obtaining a target protein through separate secretion do not exist, processes for extracting a protein from storage organ or an inner part of cells are primarily needed. A process for obtaining the target protein from the transformed cell is not easily performed. Accordingly, a method for recombining a target protein to include a tag rather than a wild-type one has been largely used to easily obtain the protein.

A method using a tag for purification is one of methods in which significantly high efficiency is exhibited among various protein purification technologies, wherein the tag to be used is largely classified into a peptide tag and a protein tag.

The peptide tag consists of short amino acids and includes a his-tag (histidine-tag) as a representative one. Particularly, a hexahistidine tag (His6-tag) has been largely used. Histidine peptide has specific chemical affinity to nickel, such that fusion proteins including corresponding tags are possible to be refined with high purity by column including nickel. The protein tag is a tag including corresponding domains, and the like, in order to use characteristics, and the like, of domains of proteins bound to specific components. The protein tag includes a GST-tag (Glutathione S-transferase-tag). The GST tag may be refined with high purity by column using glutathione which is a substrate of GST as a fixing media.

The tag fused and expressed in the target protein for protein purification as described above may have a risk of interrupting structure or function of the target protein itself, such that a method for obtaining the target protein from which the tag is cleaved has been considered. Meanwhile, the conventional method requires a primary process for obtaining a protein including a tag, a process for cleaving the tag, and a process for purifying a target protein only. During these processes, the target protein is lost, an amount of finally obtained protein is decreased, and cost and time for corresponding processes are also excessive. Accordingly, it is required to develop a method for minimizing the loss of the target protein in the process for cleaving the tag, and purifying the protein rapidly, while maintaining advantages of the method for purifying a protein using the tag.

Under this background, a method for purifying a protein using domain of Sortase A having cleaving function protein having self-cleaving function and cleavage site sequence recognized by the corresponding domain was developed (Mao H et al., Protein Expr. Purif. 2004; 37(1):253-63). The Sortase A (SrtA, 60-206 A.A.) is an enzyme which recognizes the cleavage site sequence (LPXTG, X is an any amino acid) in circumstance in which there are calcium and triglycine to generate a catalytic reaction which cuts between threonine (T) and glycine (G). The method for purifying a protein using the conventional Sortase A is a method including a step of producing a recombinant expression vector including polynucleotide encoding a tag-Sortase A(60~206 A. A.)-LPXTG-a target protein, expressing the protein in a host cell, and binding host cell pulverized product to a tag binding column; a step of removing impurities; a step of injecting calcium and/or triglycine-containing solution and performing a reaction; and a step of obtaining the protein to be capable of purifying the protein and removing a tag at a time with the use of the column only once. However, the method of using the conventional domain in Sortase A having cleaving function has a problem in that purification efficiency is low, according to a target protein.

Therefore, the present inventors has completed the present invention by confirming that remarkable protein yield is possibly obtained by focusing on a direction of binding the domain in Sortase A having cleaving function in a fusion protein and applying a linker between the Sortase A and site of sequence for cleavage, as compared the conventional method.

SUMMARY OF INVENTION

An object of the present invention is to provide a self-cleaving fusion protein including a peptide consisting of amino acid sequence represented by LPXTG, a domain of Sortase A having cleaving function, and a tag, which are sequentially positioned from the amino terminal.

Another object of the present invention is to provide a nucleic acid including nucleotide sequence encoding the fusion protein and an expression vector including the nucleic acid.

Another object of the present invention is to provide a cell transformed with the expression vector.

DESCRIPTION OF DRAWINGS

FIG. 1 shows a structure of the conventional fusion protein in which a target protein is positioned in a carboxyl terminal (I), and structures of fusion proteins according to the present invention in which target proteins are present in amino terminals and linkers have different length to each other (II: SEQ ID NO: 5; III: SEQ ID NO: 6; IV: SEQ ID NO: 7). LPETG is represented by SEQ ID NO: 59.

FIG. 2 shows a structure of a fusion protein to which a flexible linker (SEQ ID NO: 5) is added (I) or a structure of a fusion protein to which a helical linker (SEQ ID NO: 1) is added (II), for optimization of a peptide linker.

FIG. 3 shows a structure of a fusion protein to which a charged linker (a CH linker (SEQ ID NO: 2) or an AH linker (SEQ ID NO: 3)) is added, for optimization of a peptide linker.

FIG. 4 shows structures of fusion proteins that are dependent on length of a linker, linker is added or not, and a tag. "Linker (7A.A)," "Linker (18A.A)," "Linker (20A.A)," and "LPETG" are represented by SEQ ID NO: 5, SEQ ID NO: 6, SEQ ID NO: 7, and SEQ ID NO:59, respectively.

FIG. 11 shows comparison in yield of obtaining a cleaved protein depending on the presence or absence of calcium and triglycine and various concentrations, for optimization of a cleavage-buffer.

FIG. 16 shows results of analyzing concentration (A) and reaction time (B) of a triglycine-biotin conjugate in order to establish optimum conditions for conjugating the target protein to a drug.

FIG. 17 shows a process of preparing an antibody-drug conjugate (ADC) by performing a conjugate reaction of the self-cleaving cassette included fusion protein including the 'antibody-linker-Sortase' with triglycine-drug (GGG-drug) in the cleavage-buffer.

BEST MODE

Figure 5:
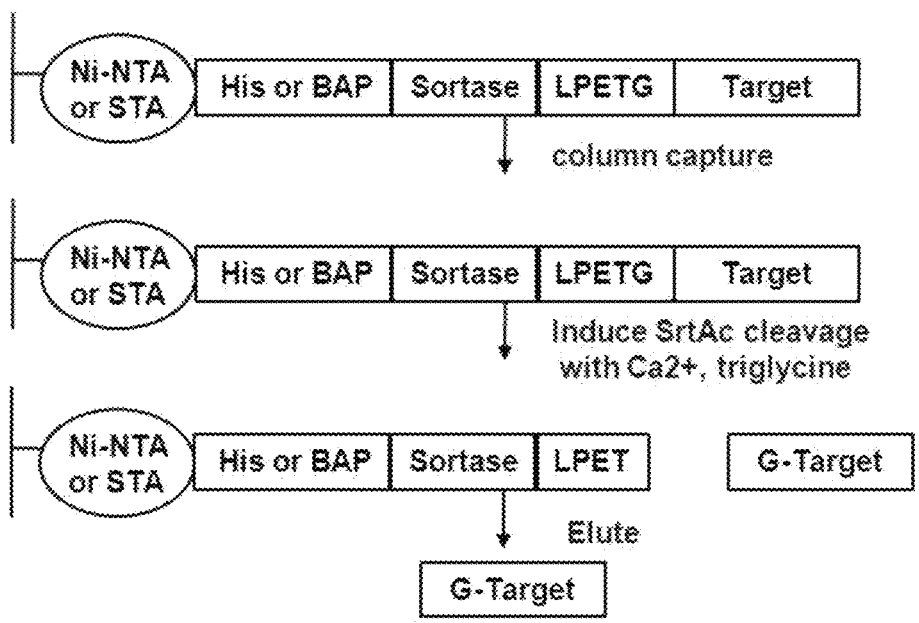
FIG. 5 is a diagram showing the method for purifying a protein using the conventional Sortase A self-cleaving cassette.

As far as it is not defined in other ways, all technical and scientific terms used in the present specification have the same meaning as being generally appreciated by those skilled in the art to which the present invention pertains. In general, a nomenclature used in the present specification and experimental methods to be described below are well known in technical fields and generally used.

As an exemplary embodiment of the present invention for achieving the above-described objects, the present invention provides a self-cleaving fusion protein including a target protein, a peptide consisting of amino acid sequence represented by LPXTG, a domain of Sortase A having cleaving function, and a tag.

Specifically, the self-cleaving fusion protein of the present invention includes:

(i) a target protein;
(ii) a peptide represented by Formula I below:

$$L\text{-}P\text{-}X\text{-}T\text{-}G;\qquad\qquad\text{[Formula I]}$$

(iii) a domain of Sortase A having cleaving function, and
(iv) a tag, wherein (i) to (iv) are sequentially positioned from an amino terminal to a carboxyl terminal of the fusion protein, and in Sequence Formula 1, L represents Leucine, P represents Proline, X represents an any amino acid, T represents Threonine, G represents Glycine.

The conventional self-cleaving fusion protein including the domain in Sortase A having cleaving function includes a target protein at a carboxyl terminal; however, there are cases in which purification yield is significantly low according to the target protein. In the present invention, it may be confirmed that an efficiency of binding of the fusion protein to a column and a cleaving efficiency are significantly improved, and thus the purification yield of obtaining the target protein is remarkably increased (FIG. 15), by positioning the target protein at an amino terminal of the Sortase A.

Preferably, the self-cleaving fusion protein of the present invention may further include a peptide linker between a peptide consisting of amino acid sequence represented by LPXTG and a domain of Sortase A having cleaving function.

The "target protein" herein refers to any protein which is required to be obtained with high purity or in a large amount for specific purposes, and includes, without limitation, a wild-type protein, a protein variant, a novel recombinant protein, and the like. The target protein may be a protein required to be obtained with high purity or in a large amount for industrial, medical, scientific reasons, and the like, preferably, may be a recombinant protein for pharmaceutical or research, and more preferably, may be selected from the group consisting of polymer proteins, glycoproteins, cytokines, growth factor, blood preparations, vaccines, hormones, enzymes and antibodies. More preferably, the target protein may be an entire portion of a light chain or a heavy chain of an antibody, or a portion thereof, and the most preferably, the target protein may be a light chain variable region (VL) or a heavy chain variable region (VH) of an antibody.

The "peptide consisting of amino acid sequence represented by LPXTG" refers to a peptide consisting of amino acid sequence of Leucine-Proline-any amino acid-Threonine-Glycine, which is a recognition sequence for Sortase A having a protein cleaving function. That is, the Sortase A recognizes the LPXTG sequence, which cleaves between Threonine and Glycine, such that a portion including LPXT and a portion including G are separated. X in the peptide consisting of LPXTG amino acid sequence in the present invention may be any amino acid, for example, may be Glutamic Acid (E).

The "Sortase A (Srt A)" in the present invention is a protein having a function of attaching a surface protein to a cell wall of gram positive bacteria, which is known to link a free carboxyl group of Threonine to a free amino group of pentaglycine in cell wall and the like, by cutting between Threonine and Glycine of LPXTG sequence.

Basically, the Sortase A is a peptidase having a function of recognizing and cleaving LPXTG sequence. The Sortase A or Srt A, and the like, in the present invention may refer interchangeably to a domain having cleaving function in Sortase A and the whole protein. In the present invention, any domain of Sortase A having cleaving function may be used. Preferably, the Sortase A may be derived from bacteria, for example, *Staphylococcus aureus* (*S. aureus*), and more preferably, the domain having cleaving function in Sortase A may consist of amino acid sequence of SEQ ID NO: 8.

The "tag" in the present invention refers to amino acid sequence, a peptide, or a protein domain, and the like, which is inserted to a recombinant protein with the purpose of labeling or obtaining a protein, and a method for purifying a protein using the tag is one exhibiting significantly high efficiency among various protein purification technologies. For this case, the tag to be used is classified into a peptide tag and a protein tag. For example, the tag in the present invention may be selected from the group consisting of a polyhistidine tag, a GST tag (glutathione-S-transferase tag), a HA tag (hemagglutinin tag), a FLAG tag, a Myc tag, a maltose binding protein tag, a chitin binding protein tag, and a fluorescent tag, but is not limited thereto. Preferably, the tag may be a polyhistidine peptide tag, more preferably a peptide tag including 6 to 12 histidines, and the most preferably, a polyhistidine peptide tag including 10 histidines.

The tag serves to attach the tag linked entire fusion protein to a column, in which a tag would be bound thereto. Accordingly, ultimately, the target protein included in the fusion protein may be obtained.

The "self-cleaving fusion protein" in the present invention refers to a protein including a domain having cleaving function and a recognition sequence recognized and cleaved by the domain in one fusion protein at the same time. Under a predetermined condition, the domain having cleaving function is activated to recognize and cleave the recognition sequence in the same protein. In the present invention, the fusion protein may include a Sortase A-derived domain having cleaving function and LPXTG recognized by the domain, and further include other constitutions.

The "self-cleaving cassette" in the present invention refers to a domain set including the domain having cleaving function and the recognition sequence recognized and cleaved by the domain, preferably, may be a domain set including the Sortase A-derived domain having cleaving function and LPXTG recognized by the corresponding domain.

The "peptide linker" in the present invention is a peptide used to have physical and chemical distance or connection between the domain and the domain in the fusion protein. The fusion protein of the present invention may include a linker between the Sortase A and the LPXTG peptide. The linker may be a natural linker, a flexible linker, a helical linker, a charged linker (a CH linker or an AH linker) or a coiled coil linker, and the like. The flexible linker in the present invention may generally have a form of (GaSb)n (a is 1 to 10, b is 1 to 10, n is 1 to 10), in particular, may include (G4S) sequence.

In the amino acids of amino acid sequence in the present invention represented by one letter abbreviations, which are conventionally used in the related art. Basically, the flexible linkers do not have a characteristic of repulsion or integration among amino acids present in the linker with each other, and thus exhibit flexible movement. The helical linker in the present invention may include General Formula of A(EAAK)mA (wherein m is 2~5), and may be 50 A.A. of (H4)2 linker (LEA(EAAAK)4ALEA(EAAAK)4AL, SEQ ID NO: 1). The charged linker in the present invention may be a positively or negatively charged linker, and a positively charged linker may be a CH linker (TRARL-SKELQAAQARLGADMEDVCGRLVQYRG, SEQ ID NO: 2), and an negatively charged linker may be an AH linker (KEQQNAFYEILHLPNLNEEQRNGFIQSLKDDP-SQSANLLAEAKKL, SEQ ID NO: 3).

The coiled coil linker may be a linker having a binding ability to other coiled coil domain or linker, while maintaining a helical three-dimensional structure, which may be one of SEQ ID NO: 9 to 16 or SEQ ID NO: 48 to 55.

Preferably, the peptide linker in the present invention may be a flexible linker, and may have a form of Sc(SG4)1(GGSSRSS)GdSe (SEQ ID NO: 4). In Sc(SG4)1(GGSSRSS)GdSe, c represents 0 to 5, d represents 0 to 5, e represents 0 to 5, and l represents 0 to 10. In the present invention, a length of the peptide linker is not important, and the length of the linker may vary depending on target proteins for accessibility of an active site. Preferably, the linker may consist of 19 to 40 amino acids, and more preferably, 19 to 25 amino acids. The most preferably, the linker may be a peptide linker consisting of amino acid sequence represented by SEQ ID NO: 7.

When the target protein is an antibody variable region in a specific exemplary embodiment of the present invention, linker optimization was tested by changing length of the linkers, the number of linkers, and types of linkers, in order to confirm an effect of the linker on yield of obtaining the target protein.

When comparing yields of obtaining the target proteins (Examples 5-1, FIGS. 9 and 10) among linkers with different lengths, 7 A.A.(SEQ ID NO: 5), 18 A.A.(SEQ ID NO: 6) and 20 A.A.(SEQ ID NO: 7), it was confirmed that yield of obtaining the target protein was increased in case of including the linker with the length of 20 A.A.

Figure 13:
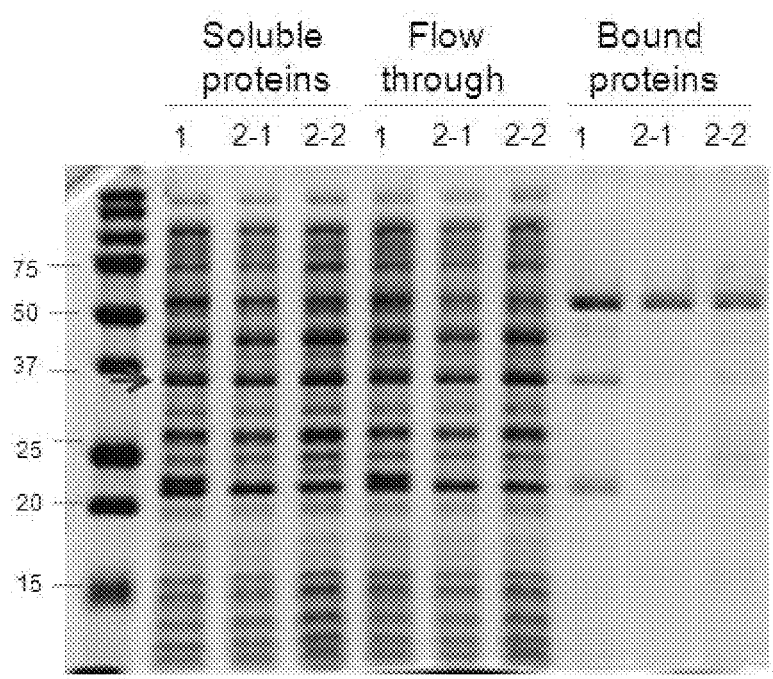
FIG. 13 shows results of confirming level of expression and binding of a fusion protein with the flexible linker (7 A.A.) between domain in Sortase A having cleaving function and a tag (2-1 or 2-2) and a fusion protein without the flexible linker (1).

Meanwhile, an effect on yield of obtaining the target protein from decrease interference between the domains (Example 5-2) was evaluated by further including a linker between the domain in Sortase A having cleaving function and the tag, in addition to the linker between LPXTG recognition sequence and domain in Sortase A having cleaving function (FIG. 2). Specifically, (1) a protein from a cell transformed with a vector expressing a fusion protein having a structure of target protein (VH)-LPETG-linker(20 A.A.)-Sortase A-His tag was compared with (2) a protein from a cell transformed with a vector expressing a fusion protein having a structure of target protein (VH)-LPETG-linker(20 A.A.)-Sortase A-linker(7 A.A.)-His tag (FIG. 13). In case of (1), proteins bound to the column were confirmed (Bound proteins); however, in case of (2), proteins bound to the column were hardly found. That is, the addition of the linker to C-terminal of Sortase A did not lead to an increase in binding of the fusion protein to column.

Figure 12:
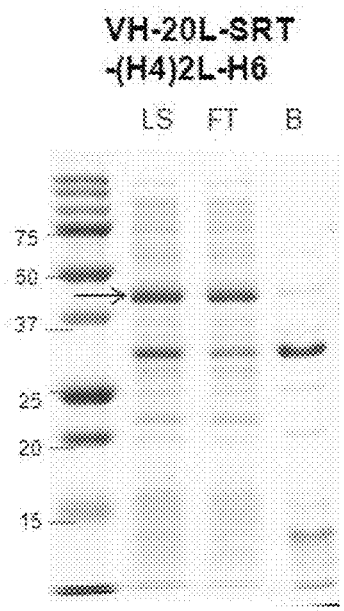
FIG. 12 shows results of confirming level of expression and binding of the fusion protein in case of adding a helical linker thereto.
Figure 14:
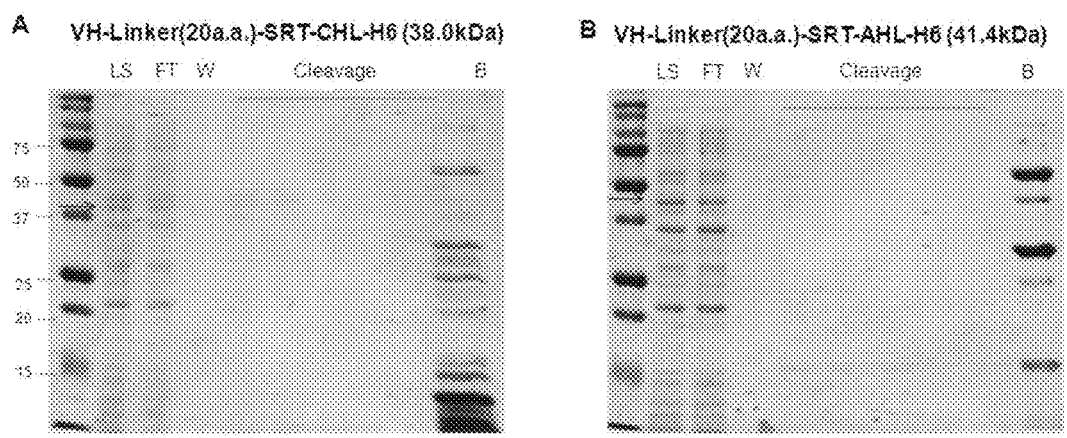
FIG. 14 shows results obtained by confirming expression, binding, and purification degrees of the fusion protein to which the charged linker (a CH linker or an AH linker) is added.

An effect on yield of obtaining the target protein in a case in which the helical linker or the charged linker as listed above as the types of the linkers is inserted between the domain in Sortase A having cleaving function and the tag was confirmed (Example 5-3, FIGS. 12 and 14). Specifically, it could be confirmed that the fusion protein was hardly bound to the column (FIG. 12) in a case of which the helical linker is additionally inserted between the domain in Sortase A having cleaving function and the tag, while remaining the flexible linker (20 A.A.) between the LPXTG recognition sequence and the domain in Sortase A having cleaving function.

In addition, even in a case in which the charged linkers such as the positively charged linker (CH linker, SEQ ID NO: 2) or the negatively charged linker (AH linker, SEQ ID NO: 3) are additionally inserted between the domain in Sortase A having cleaving function and the tag, while remaining the flexible linker (20 A.A.) between the LPXTG recognition sequence and the domain in Sortase A having cleaving function, it could be confirmed that the fusion protein was hardly bound to the column, and the cleavage protein was hardly found (FIG. 14).

The self-cleaving fusion protein of the present invention may comprise amino acid sequence represented by SEQ ID NO: 17 or 18. This refers to the fusion protein includes an antibody variable region as the target protein, LPETG recognition sequence, a peptide linker, a domain of Sortase A having cleaving function (60~206 A.A.) and a tag for binding to column (His9) sequentially from the amino terminal.

According to another exemplary embodiment of the present invention, there is provided a nucleic acid including nucleotide sequence encoding the self-cleaving fusion protein of the present invention. The nucleotide sequence encoding the fusion protein of the present invention may be a nucleotide sequence encoding amino acid sequence of SEQ ID NO: 17 or 18, preferably, SEQ ID NO: 56 or 57.

According to another exemplary embodiment of the present invention, there is provided an expression vector including the nucleic acid as described above.

The "expression vector" in the present invention refers to a vector operably linked with a promoter, and the like, to express specific genes in specific prokaryotic or eukaryotic host cells. A backbone of the vector may be changed depending on the host cells. The vector of the present invention may be a vector which is possible to be expressed in *E. coli*, more preferably, pET21b, pLIC, pET23a vectors (Novagen).

According to another exemplary embodiment of the present invention, there is provided a cell transformed with the expression vector as described above.

The cell to be a target for transformation refers to a host cell, and includes eukaryotic or prokaryotic host cells. In the present invention, the host cell may be preferably *Escherichia coli*, and more preferably, *E. coli* Origami2(DE3) or *E. coli* BL21(DE3) strains.

Figure 9:
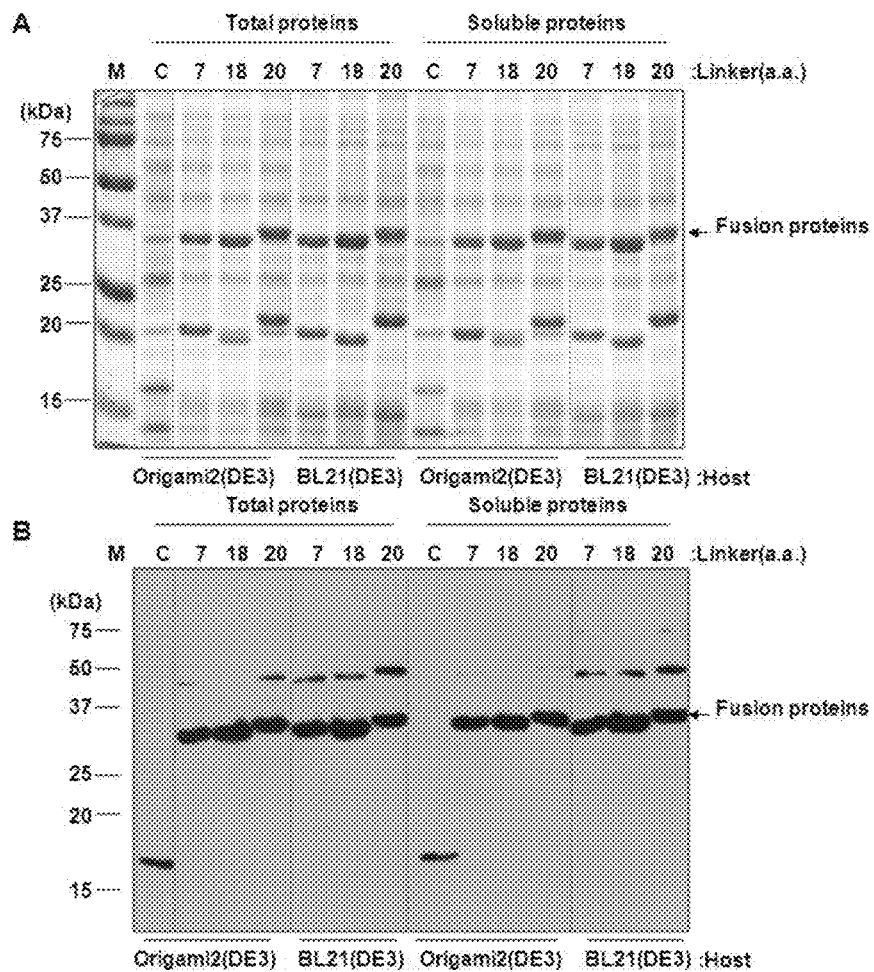
FIG. 9 shows degree of expression on fusion proteins from various *E. coli* host cells (Origami2(DE3), and BL21 (DE3) transformed with expression vectors including the Sortase A self-cleaving cassette according to the present invention and linkers with different length (7, 18, 20 A.A.).

According to specific exemplary embodiment of the present invention, aspects showing transformation and expression of *E. coli* Origami2(DE3) and *E. coli* BL21(DE3) as the host cells transformed with the expression vectors of the present invention were compared (FIG. 9). As confirmed in FIG. 9, there was no big difference in expression aspects between Origami2 and BL21.

According to another exemplary embodiment of the present invention, there is provided a method for purifying a target protein including: culturing cells of the present invention to obtain cell lysates; and purifying the target protein from the cell lysates.

In addition, preferably, the purifying of the target protein from the cell lysates may include: injecting the cell lysates into a column bound to a tag in a fusion protein; washing the column; equilibrating the column by using a cleavage buffer including at least one selected from the group consisting of calcium and triglycine to perform a cleaving reaction; and obtaining the cleavage-buffer from the column to obtain the target protein from which the tag is removed.

The "column" in the present invention is an apparatus performing functions of isolating and/or purifying specific components, proteins, and compounds while injecting a mixture solution including the specific component, proteins, and compounds and allowing the mixture solution to pass through inside of the column. In the present invention, particularly, the column functions to isolate and refine the compounds, the components, the proteins, and the like, by fixing the compounds, the components, the proteins, and the like, having a binding property to the specific tag included in the fusion protein to the inside of the column to thereby attach the proteins having the tag to the inside of the column. When the tag included in the fusion protein is His-tag (tag including histidine), a Ni-NTA column using a binding property to nickel may be used, and when the tag included in the fusion protein is GST, a column including Glutathione as a fixing media may be used.

The "cleavage-buffer" in the present invention indicates a buffer activating a domain having cleaving function, in particular, a buffer activating Sortage A. The cleavage-buffer may include calcium and/or triglycine, preferably, may include at least triglycine. In addition, the cleavage-buffer may preferably include 0.1 to 10 mM of calcium and 0.1 to 10 mM of triglycine, and more preferably, 0.2 to 5 mM of calcium and 0.2 to 5 mM of triglycine.

In a specific exemplary embodiment of the present invention, yield of obtaining the cleavage protein was confirmed by including or not including calcium or triglycine and by changing concentration conditions in order to confirm optimum conditions of the cleavage reaction. Yield of obtaining the cleavage protein by the cleavage-buffer in which one of calcium and triglycine having a concentration to be fixed as 5 mM and the remaining other one having a concentration of 0, 0.2, 1, or 5 mM are mixed is compared with that of a negative control group without including both of calcium and triglycine. In the negative control group, the cleaved protein could not be observed at all (about 15 kDa), and in a case if one of calcium and triglycine is included, the cleavage protein could be observed. In addition, it could be confirmed that in a case of including a certain amount of triglycine and controlling concentration of calcium, there was little difference in an amount of cleaved protein to be obtained. However, in a case of including a certain amount of calcium and controlling concentration of triglycine, in particular, the cleaved protein was obtained in a small amount, when triglycine is not included. It was confirmed that triglycine included in the cleavage-buffer has an important role in cleavage function of Sortase.

The "therapeutic antibody-drug conjugate (ADC)" in the present invention consists of three components including a drug, an antibody, and a linker linking the drug and the antibody, and the therapeutic antibody-drug conjugate technology is a method in which the drug is delivered to tumor cells by using the antibody specifically bound to a specific antigen expressed on the surface of cancer cells.

The therapeutic antibody-drug conjugate may be prepared according to the present invention. Specifically, in order to build a self-cleaving cassette including 'antibody-linker-Sortase' at the amino terminal, and recognize cleavage sequence (LPXTG) and perform cleavage function by Sortase A, calcium and/or triglycine are required, wherein the drug is linked to C-terminal of triglycine which is a derivative inducing this cleavage and the reaction is performed. When 'triglycine-drug (GGG-drug)' linking the drug to C-terminal of triglycine is prepared or synthesized, and then is used for the cleavage reaction of the self-cleaving cassette including the constructed 'antibody-linker-Sortase', an 'antibody-linker-drug (antibody-linker-LPETGGG-drug)' may be prepared by an optimized cleavage reaction.

Specifically, the drug usable for the therapeutic antibody-drug conjugate of the present invention may include any compound having an effect for inhibiting cytotoxicity or cell proliferation, a portion or a group, and includes:
  (i) chemotherapeutic agent capable of functioning as a microtubulin inhibitor, a mitotic inhibitor, a topoisomerase inhibitor, or a DNA Intercalator;
  (ii) a protein toxin capable of functioning as an enzyme;
  (iii) micro RNA (miRNA), siRNA, shRNA capable of inhibiting expression of specific carcinogenic gene (oncogene); and
  (iv) a radioactive isotope, and the like.

The drug may include various antitumor or anticancer agents including maytansinoid, auristatin, dolastatin, tricotecene, CC1065 (cytotoxic compound), calicheamicin and other enediyne antibiotics, taxane, anthracycline, methotrexate, adriamycin, vindesine, vinca alkaloids (vincristine, vinblastine, etoposide), doxorubicin, melphalan, mitomycin C, chlorambucil, daunorubicin, daunomycin and stereoisomers thereof, isosters, analogs or derivatives thereof, enzymes as other insertion agents and fragments thereof, such as nucleolytic enzymes, antibiotics, and toxins (bacteria, fungi, plants or animals-origin enzymatically active toxins or small molecule toxins) and cisplatin, CPT-11, doxorubicin, paclitaxel and docetaxel, and the like, but the present invention is not limited thereto.

In a specific exemplary embodiment of the present invention, yield of obtaining the cleavage protein was confirmed by including or not including triglycine-biotin and by changing concentration conditions in order to confirm optimum conditions of the cleavage reaction for preparing a therapeutic antibody-drug conjugate. Yield of obtaining the target protein by the cleavage-buffer was compared with that of a negative control group, by including triglycine-biotin at a concentration of 0, 10 nM, 100 nM, 500 nM, 1 μM, 10 μM, 100 μM, 500 μM, 1 mM. In the negative control group, binding of the target protein to biotin could not be observed at all (about 45 kDa), and a large amount of binding reaction could be observed at a concentration of 500 μM to 1 mM. Optimum reaction time condition of the cleavage reaction was confirmed by using the concentrations of triglycine-biotin as established above. Yield of obtaining the target protein-biotin conjugate after performing the reaction for 0, 30 minutes, 1, 2, 3, 4, 6 hours, and 16 hours, was compared with that of a negative control group. A large amount of triglycine-biotin could be observed in the binding reaction performed for 4 to 16 hours.

In addition, the cleavage-buffer preferably includes 0.1 to 10 mM calcium and 500 nM to 1 mM triglycine-drug (GGG-drug), but the present invention is not limited thereto. Time required for the binding the target protein to triglycine-drug (GGG-drug) is preferably 4 to 16 hours, but the present invention is not limited thereto.

The target protein is preferably an antibody to against a tumor surface antigen, but the present invention is not limited thereto.

Hereinafter, the present invention will be described in detail with reference to the following Examples. These examples are only for exemplifying the present invention, and it will be obvious to those skilled in the art that the scope of the present invention is not construed to be limited to these examples.

EXAMPLE 1

Construction of Expression Vector 1-1: PCR Reaction Solution and Conditions

A composition of PCR reaction solution and PCR performance conditions for obtaining various genes and constructing vectors used in the present invention were as follows.

Firstly, the PCR reaction solution (50 μl) was prepared by including 2.5 mM dNTP mix (5 μl), 5× PrimeSTAR buffer (10 μl), 100 μM forward and reverse primers (respectively 1 μl), 100 ng/uL of template DNA (1 μl), 2.5 U/uL PrimeSTAR polymerase (0.5 μl) and distilled water (31.5 μl).

The prepared PCR reaction solution was used to perform two-step PCR which repeats a cycle 29 times, wherein the cycle includes a step at 98° C. for 10 seconds and a step at 68° C. for 1 minute. Samples obtained after PCR was completed were stored at 4° C.

1-2: Preparation of BAP-Sortase-LPETG-target (VL)

Firstly, DNA sequence encoding BAP(biotin acceptor peptide) was amplified by PCR by using a primer 1_sfi (5'-ccgtg gcc cag gcg gcc GCA AGC AGC GGC CTG AAC GAC ATC TTCGAG GCC-3': SEQ ID NO: 19) or a primer 1 (5'-ATGT CAT ATG GCA AGC AGC GGC CTG AAC GAC ATC TTC GAG GCC-3': SEQ ID NO: 20), and a primer 2 (5'-CTG CAT TTC GTG CCA CTC GAT CTT CTG GGC CTC GAA GAT GTC GTT-3': SEQ ID NO: 21).

DNA sequence encoding 60th to 206th amino acid sequences of Staphylococcus aureus (S. aureus)-derived SrtA(GenBank Accession No. AF162687) was amplified by PCR by using a primer 3 (5'-ATC GAG TGG CAC GAA ATG CAG GCT AAG CCG CAG ATT CCG-3': SEQ ID NO: 22) and a primer 4 (5'-GCC GGT CTC GGG AAG CTT CTT GAC CTC GGT AGC GAC AAA-3': SEQ ID NO: 23).

Secondary DNA sequence encoding LPETG-target (VL) was amplified by PCR by using a primer 5 (5'-CAG TAA GCT TCC CGA GAC CGG CGG CGA TAT CCA GAT GAC TCA GAGC-3': SEQ ID NO: 24), a primer 6 (5'-ACT CGA ACC CGC CGT ACG TTT TAT CTC TAC CTT TGT-3': SEQ ID NO: 25) and a template target (VL).

Then, after three PCR products prepared as above were mixed with each other, DNA sequence encoding BAP-SrtA-kLPETG-target (VL) which is a fusion protein having Hind III site between SrtAc-LPETG and sequence encoding a target was amplified by PCR by using the primer 1_sfi or the primer 1 and the primer 7 (5'-taatggccggcctggcc GCG GCC GCT TAA AGA TCT TCT TCA CTA ATT AACTT-3': SEQ ID NO: 26).

DNA fragments resulted therefrom were cleaved by NdeI and NotI, the target protein was ligated with a pET23a vector (Novagen) inducing expression into cytoplasm, cleaved by SfiI, and BAP-Sortase-LPETG-target-myc (I in FIG. 1) which is a fusion protein was ligated with pCom3× which is a vector inducing expression into periplasm.

1-3: Preparation of Target (VL)-kLPETG-linker-Sortase-H9

DNA sequence encoding target-LPETG-linker (7 A.A.) linked with a linker (7 A.A.) (GGSSRSS: SEQ ID NO: 5) was amplified by PCR by using a primer 8 (5'-ATG TCA TAT GGA CAT TCA GAT GAC ACA GAGT-3': SEQ ID NO: 27) and a primer 9 (5'-ggaaccaccgccggtctcgggaag AAG ATC TTC TTC ACT AAT TAAC-3': SEQ ID NO: 28).

DNA sequence encoding target-LPETG-linker (18 A.A.) linked with a linker (18 A.A.) (SSGGGGSGGGGGGSSRSS: SEQ ID NO: 6) was amplified by PCR by using a primer 8 and a primer 10 (5'-GGA AGA TCT AGA GGA ACC ACC CCC ACC ACC GCC CGA GCC ACC GCC ACC GGA TGA GCC GGT CTC GGG AAG AAG AT-3': SEQ ID NO: 29) and a target-LPETG-linker (7 A.A.) which is the product obtained by PCR above.

DNA sequence encoding linker (7 A.A.)-SrtA(60-206) was amplified by PCR by using a primer 11 (5'-gag acc ggc ggt ggt tcc tct aga tct tcc cag gct aag ccg cag att-3': SEQ ID NO: 30) and a primer 12 (5'-taat GC GGC CGC tta atgatggtg ATG GTG ATG ATG ATG ATGGC-3': SEQ ID NO: 31).

DNA sequence encoding linker(18 A.A.)-SrtA(60-206) was amplified by PCR by using a primer 13 (5'-gtggttcctcta-gatcttcc TCG AAG GTC GCG GGA TAT ATT-3': SEQ ID NO: 32) and a primer 14 (5'-taatggccggcctggcctta atgatggtg ATG GTG ATG ATG ATG ATG GC-3': SEQ ID NO: 33).

DNA sequence encoding a linker (20 A.A.)-SrtA(60-206) with a linker (20 A.A.) (SSGGGGSGGGGGGSSRSSGS: SEQ ID NO: 7) was amplified by PCR by using a primer 15 (5'-GGT TCC TCT AGA TCT TCC GGA AGC cag gct aag ccg cag att-3': SEQ ID NO: 34) and the primer 14.

DNA sequence encoding linker (20 A.A.)-SrtA(60-206)-linker (7 A.A.) with a linker (20 A.A.) (SSGGGGSGGGGGGSSRSSGS: SEQ ID NO: 7) linked to N-terminal, and a linker (7 A.A.) (GGSSRSS: SEQ ID NO: 5) linked to C-terminal was amplified by PCR by using the primer 15, a primer 16 (5'-ATG ATG ATG GCG AGA GCT ACG GCT GCT GCC GCC CTT GAC CTC GGT AGC GAC AAA GA-3': SEQ ID NO: 35), and a primer 17 (5'-TAA TGC GGC CGC TTA ATG ATG GTG ATG GTG ATG ATG ATG ATG GCG AGA GCT ACG GCT-3': SEQ ID NO: 36).

DNA sequence encoding linker (20 A.A.)-SrtA(60-206)-(H4)2L linker (50 A.A.) with a linker (20 A.A.) (SSGGGGSGGGGGGSSRSSGS: SEQ ID NO: 11) linked to N-terminal, and a (H4)2L linker (50 A.A.)(SEQ ID NO: 1) linked to C-terminal was amplified by PCR by using the primer 15, a primer 18(5'-ACG ACG ACG ACG GCG CTC CAG TGC CTT AGC AGC GGC TTC CTT AGC AGC AGC CTC CTT AGC AGC TGC TTC TTT CGC TGC GGC TTC CGC TTC CAA CGC TTT C-3': SEQ ID NO: 37), and a primer 19(5'-TAA TGC GGC CGC TTA ACG GCG ACG ACG GCG ACG ACG ACG ACG GCG CTC CAG T-3': SEQ ID NO: 38).

DNA sequence with a linker (20 A.A.) (SSGGGGSGGGGGGSSRSSGS: SEQ ID NO: 7) linked to N-terminal and encoding TRA- of N-terminal of CH linker (32 A.A.) was amplified by PCR by using the primer 15, a primer 20(5'-GTG CCC GCG TCT TGA CCT CGG TAG CGA CAA AGA TCTT-3': SEQ ID NO: 39), and the CH linker part was amplified by using a primer 21 (5'-GCT GTC CAA GGA GCT GCA GGC GGC GCA GGC CCG GCT GGG CGC GGA CAT G-3': SEQ ID NO: 40), a primer 22(5'-GCG GTA CTG CAC CAG GCG GCC GCA CAC GTC CTC CAT GTC CGC GCC CAG CCGG-3': SEQ ID NO: 41), and a primer 23(5'-GAG GTC AAG ACG CGG GCA CGG CTG TCC AAG GAG CTG CAG-3': SEQ ID NO: 42) and a primer 24(5'-TAA T GC GGC CGC TTA ATG ATG CTG ATG GTG ATG GCC GCG GTA CTG CAC CAG GC-3': SEQ ID NO: 43), and DNA sequence encoding a linker (20 A.A.)-SrtA(60-206)-CHL linker (32 A.A.) with a linker (20 A.A.)(SSGGGGSGGGGGGSSRSSGS: SEQ ID NO: 7) linked to N-terminal and a CHL linker (32 A.A.) (TRARLSKELQAAQARLGADMEDVCGRLVQYRG: SEQ ID NO: 2) linked to C-terminal was amplified by overlapping PCR by using a mixture of the primers 15 and 24 and the product obtained by PCR above (the linker (20 A.A.)-SrtA(60-206)-CHL(TRA-)) and the CHL linker (32 A.A.) (TRARLSKELQAAQARLGADMEDVCGR-LVQYRG: SEQ ID NO: 2).

DNA sequence encoding a linker (20 A.A.) (SSGGGGSGGGGGGSSRSSGS: SEQ ID NO: 11) linked to N-terminal and KEQ- of N-terminal of AH linker (45 A.A.) was amplified by using the primer 15 and a primer 25(5'-CGG ATC ACC CTT GAC CTC GGT AGC GAC AAA GAT CTT-3': SEQ ID NO: 44), and AH linker was amplified by using a primer 26 (5'-GAG GTC AAG GGT GAT CCG AAA GCT GAC AAC AAA TTC-3': SEQ ID NO: 45) and a primer 27 (5'-GTG ATG ATG ATG ATG GTG AGC TTT TGG TGC TTG TGC ATC AT-3': SEQ ID NO: 46), and using pIG20 vector as a template. DNA sequence encoding a linker(20 A.A.)-SrtA(60-206)-AHL linker (45 A.A.) with an AH linker (45 A.A.) (KEQQNAFYEILHLPN-LNEEQRNGFIQSLKDDPSQSAN LLAEAKKL: SEQ ID NO: 3) linked to C-terminal was amplified by overlapping PCR by using a mixture of the primer 15, a primer 28 (5'-IAA T GC GGC CGC TTA ATG ATG GTG ATG GTG ATG ATG ATG ATG GTG AGC TTT TGG-3': SEQ ID NO: 47) and the product obtained by PCR above (linker(20 A.A.)-SrtA(60-206)-AHL(KEQ-)) and AHL linker (45 A.A.) (KEQQNAFYEILHLPNLNEEQRNGFIQSLKDDP-SQSANLLAEAKKL: SEQ ID NO: 3).

Lastly, target (VL)-LPETG-linker (7 A.A.)-Sortase-H9 (II of FIG. 1) was amplified by overlapping PCR by using a mixture of a primer 8, a primer 12 and the product obtained by PCR above (target-LPETG-linker (7 A.A.) and linker (7 A.A.)-SrtA).

Gene encoding target (VL)-LPETG-linker (18 A.A.)-Sortase-H9 (III of FIG. 1) was amplified by overlapping PCR by using a mixture of the primer 8, the primer 14 and the product obtained by PCR above (target-LPETG-linker (18 A.A.) and linker (18 A.A.)-SrtA).

Gene encoding target (VL)-LPETG-linker (20 A.A.)-Sortase-H9 (IV of FIG. 1) was amplified by overlapping PCR by using a mixture of the primer 8, the primer 14 and the product obtained by PCR above (target-LPETG-linker (20 A.A.) and linker (20 A.A.)-SrtA).

Gene encoding target (VL)-LPETG-linker (20 A.A.)-Sortase-linker (7 A.A.)-H9 (I of FIG. 2) was amplified by overlapping PCR by using a mixture of the primer 8, the primer 17 and the product obtained by PCR above (target-LPETG-linker (20 A.A.) and linker (20 A.A.)-SrtA-linker (7 A.A.)).

Gene encoding target (VL)-LPETG-linker (20 A.A.)-Sortase-(H4)2L linker (50 A.A.)-H9 (II of FIG. 2) was amplified by overlapping PCR by using a mixture of the primer 8, the primer 19 and the product obtained by PCR above (target-LPETG-linker (20 A.A.) and linker (20 A.A.)-SrtA-(H4)2L linker (50 A.A.))

Gene encoding target (VL)-LPETG-linker (20 A.A.)-Sortase-CHL linker (32 A.A.)-H9 (I of FIG. 3) was amplified by overlapping PCR by using a mixture of the primer 8, the primer 24 and the product obtained by PCR above (target-LPETG-linker (20 A.A.) and linker (20 A.A.)-SrtA-CHL linker (32 A.A.)).

Gene encoding target (VL)-LPETG-linker (20 A.A.)-Sortase-AHL linker (45 A.A.)-H9 (II of FIG. 3) was amplified by overlapping PCR by using a mixture of the primer 8, the primer 28 and the product obtained by PCR above (target-LPETG-linker (20 A.A.) and linker (20 A.A.)-SrtA-AHL linker (45 A.A.)).

DNA fragments resulted therefrom were cleaved by NdeI and NotI, the target protein was ligated with a pET23a vector (Novagen) which is a vector expressing target-LPETG-other linker-Sortase-R9, target-LPETG-other linker-Sortase-H6, or target-LPETG-other linker-Sortase-H9, that is the fusion protein.

Target-LPETG-other linker-Sortase-R9, target-LPETG-other linker-Sortase-H6, or target-LPETG-other linker-Sortase-H9 which is a fusion protein has HindIII site between the target and sequence encoding LPETG-other linker-Sortase-R9, LPETG-other linker-Sortase-H6, or LPETG-other linker-Sortase-H9. Then, for expression, all gene constructs were cleaved by NdeI and HindIII, and ligated with pET23a-LPETG-other linker-Sortase-R9, pET23a-LPETG-other linker-Sortase-H6, or pET23a-LPETG-other linker-Sortase-H9.

EXAMPLE 2

Confirmation of Expression in Soluble Condition

Expression tests were performed by using *E. coli* Origami2 (DE3) or BL21(DE3). Single bacterial colony was inoculated in dYT medium (30 ml) containing 100 mg/l of ampicillin and 0.5% (w/v) of glucose, and cultured overnight at 37° C. The preculture was inoculated in 0.3 l of LB, SB, or dYT medium (100 mg/l of ampicillin, 50 mM $K_2HPO_4$), and cultured at 37° C. (1 l flask with baffles, 200 rpm). When OD600 was 0.6, IPTG was added so as to have a final concentration of 0.5 mM to induce expression. The culturing was maintained at 18° C. for 18 hours. Cells were collected by centrifugation (10,000 rpm, 10 minutes, 4° C.), suspended in 30 ml of 50 mM Tris-HCl (pH 8.0) and 150 mM NaCl, and crushed by ultrasonic waves (sonication). The crude extract was centrifuged (10,000 rpm, 30 minutes, 4° C.), and the supernatant was filtered with 0.2 mm filter and applied directly to Ni FF chromatography as described in Example 3 below.

EXAMPLE 3

Ni-NTA Purification

The supernatant of the lysate was loaded on 5 ml of Ni-NTA (GE) column, and washed with a buffer. A (50 mM Tris-Cl, pH 8.0, 150 mM NaCl, 30 mM imidazole, and 5 mM BME) having a volume 20 times larger than column volume, and washed with a buffer B (50 mM Tris-Cl, pH 8.0, 150 mM NaCl) having a volume 5 times larger than column volume. After washing, aliquote of protein-binding resin was equilibrated with a cleavage-buffer (a buffer B including 5 mM $CaCl_2$ and 5 mM tri-Gly), and reacted at 25° C. for 1 hour.

Figure 8:
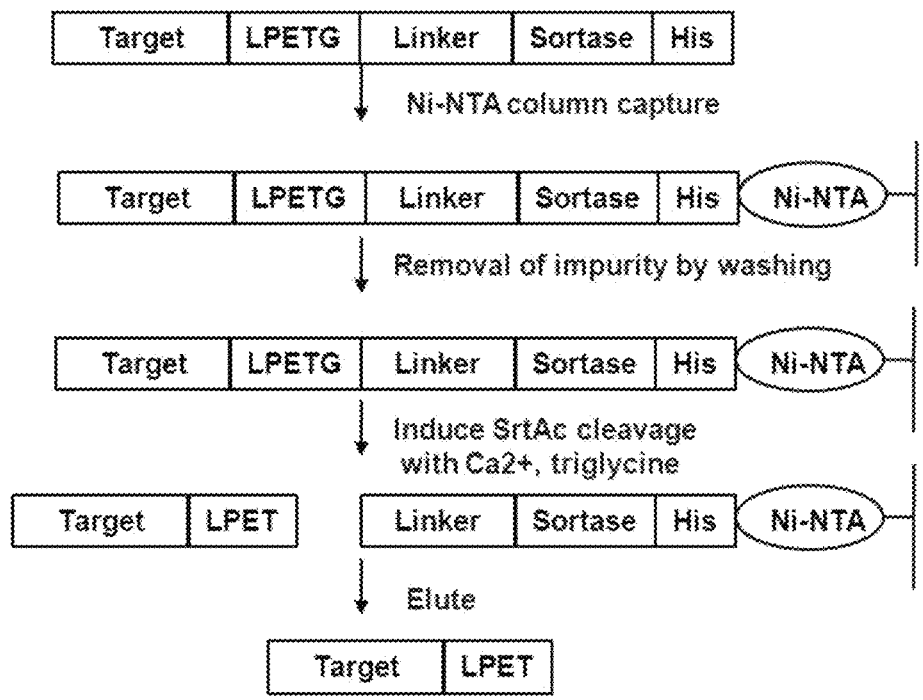
FIG. 8 is a diagram for showing a purifying method by using Sortase A self-cleaving cassette according to the present invention.

The corresponding process was progressed as shown in FIGS. 5 and 8. FIG. 5 shows a process for purifying the conventional fusion protein in which Sortase A is bound to the C-terminal shown in I of FIG. 1, and FIG. 8 shows a process for purifying the fusion protein in which Sortase A is bound to the N-terminal according to the present invention.

Protein purity was analyzed by Coomassie blue staining of SDS-PAGE gels. In addition, whether or not expression and purification were performed on some samples was confirmed by Western blotting.

EXAMPLE 4

Confirmation of Expression and Purification of Sortase Fusion Protein

When the target protein is linked to N-terminal or C-terminal of the entire fusion protein on the basis of the target protein in view of a structure of fusion proteins, change in purification efficiency was confirmed.

Whether or not expression is performed was confirmed in cell lysates obtained by Example 2 above from the host cell (*E. coli*) transformed with the expression vectors obtained by inserting the fusion protein shown in I of FIG. 1 into pET21b, pET23a, and pLIC. The cell lysates were refined by binding to Ni-NTA(GE) column as described in Example 3, and the proteins were confirmed in a state in which they were bound to the column.

The expression and the purification were confirmed by Coomassie blue staining and Western blotting using a Myc tag bound to the target protein.

Figure 6:
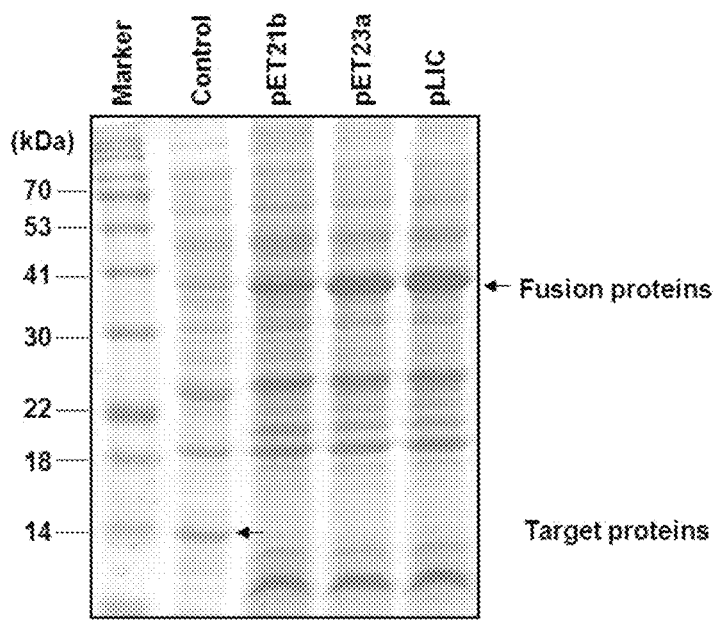
FIG. 6 shows results of staining SDS-PAGE gels with Coomassie blue for confirming expression of fusion proteins with various types of expression vectors.
Figure 7:
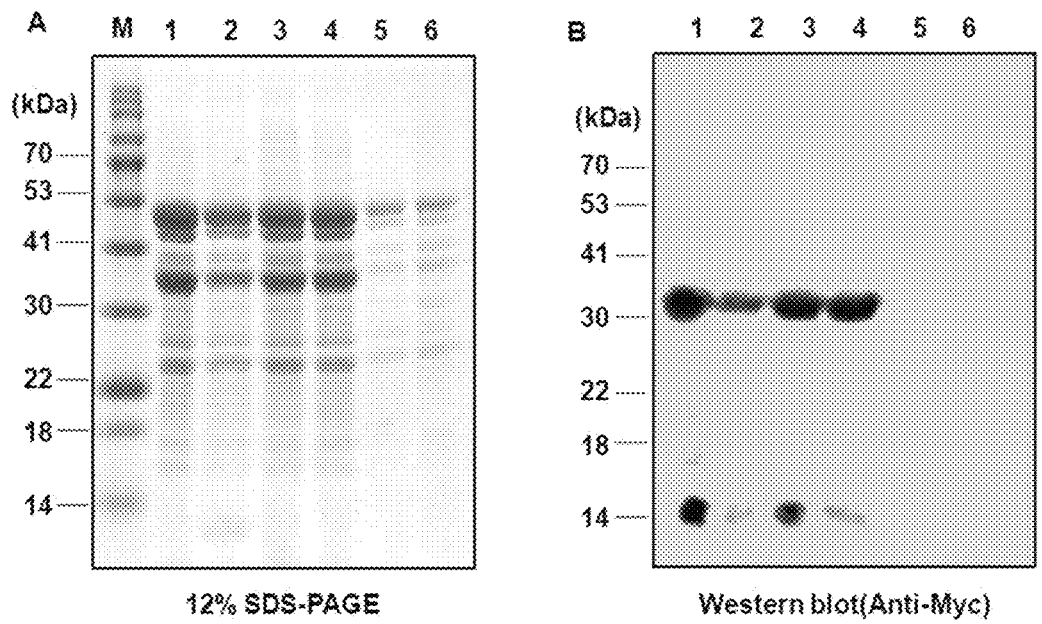
FIG. 7A shows protein expression by using the method for purifying a protein using a conventional Sortase A self-cleaving cassette.
FIG. 7B shows whether the protein is expressed (A) and the cleaved target protein (anti-Myc) is purified (5 and 6 lanes).

As shown in FIG. 6, the fusion protein was well expressed regardless of the vectors, and as shown in FIG. 7, the fusion protein including the target protein at the C-terminal could not be bound to the column, and purification activity could be rarely confirmed (5, 6 lanes in FIG. 7B).

In order to confirm an effect of a position of the target protein on the purification efficiency, the fusion proteins including the target proteins positioned at N-terminal and at C-terminal were compared with each other in view of purification efficiency. It was confirmed by experiments according to Examples 2 and 3.

Figure 15:
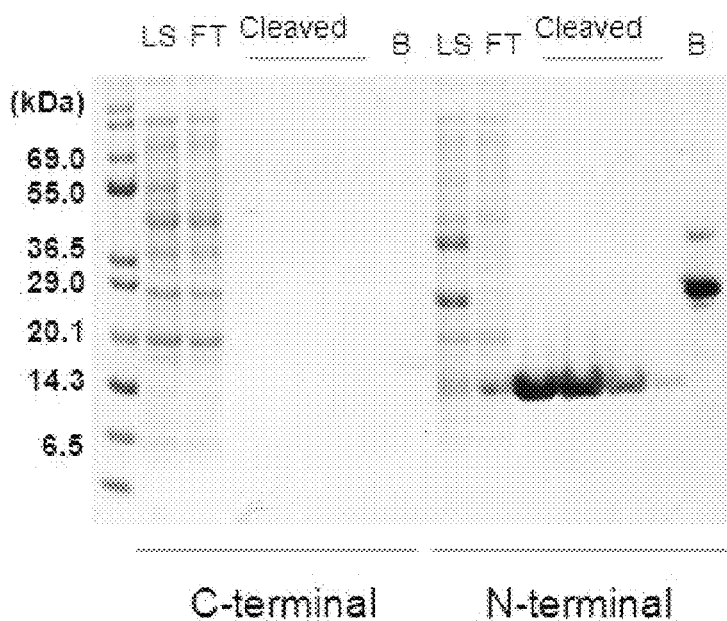
FIG. 15 shows results of confirming level of expression, binding, and purification of the fusion protein including the conventional Sortase A cleaving cassette, that is, the fusion protein including the target protein at a carboxyl terminal (C-terminal), and the fusion protein including the Sortase A cleaving cassette of the present invention, that is, the fusion protein including the target protein at an amino terminal(N-terminal).

As shown in FIG. 15, the cleaved protein (Cleaved) was not detected in the case in which the target protein was positioned at C-terminal. Meanwhile, it could be confirmed that the cleaved protein was present in significantly high purity in the case in which the target protein was positioned at N-terminal. As confirmed by comparison between Ls lane and flow through (FT) lane and by bound proteins present in the column in each case, it could be confirmed that when the target protein is positioned at C-terminal, the fusion protein could be rarely bound to the column; meanwhile, when the target protein was positioned at N-terminal, the fusion proteins had significantly high binding ratio, and most of the bound fusion proteins were cleaved.

EXAMPLE 5

Linker Optimization Test 5-1: Length Optimization of Linker

Whether or not expression is performed was confirmed in cell lysates obtained by culturing Origami2(DE3) or BL21 (DE3) transformed with vectors expressing the fusion protein shown in II to IV of FIG. 1 in LB, SB or dYT medium, and performing the method as shown in Example 2. The cell lysates were refined by binding to Ni-NTA(GE) column as described in Example 3, and the proteins were confirmed in a state in which they were bound to the column.

The expression and the purification of the target protein were confirmed by Coomassie blue staining and Western blotting using a HA tag antibody in a case of VH, and using a myc tag antibody in a case of VL.

As shown in FIG. 9, it was confirmed that expression was well achieved without showing difference between host cells (Origami2 or BL21).

Figure 10:
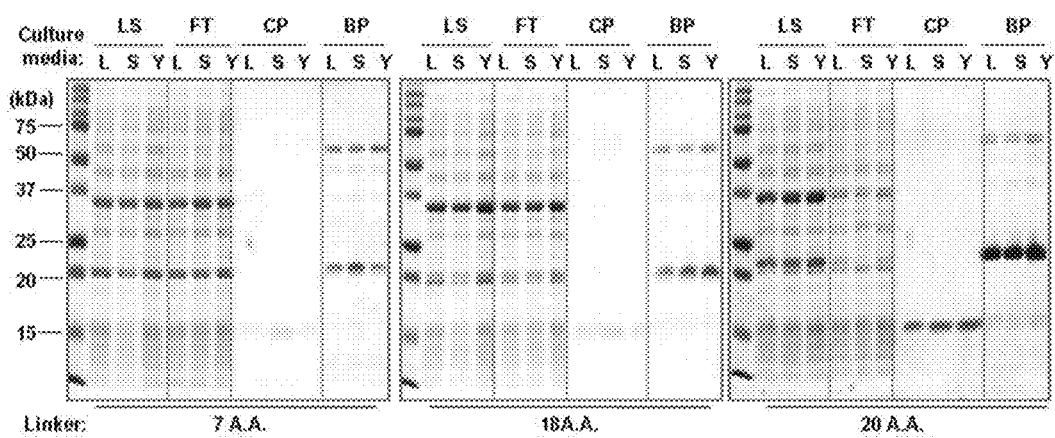
FIG. 10 shows results of confirming level of expression (LS, loading sample) by culturing the cells transformed with the expression vectors of the present invention with various linkers in LB(L), SB(S), 2×YT(Y) mediums, binding (FT, flow through; BP, bound protein) and purification (CP, cleaved protein).

In addition, as shown in FIG. 10, it may be seen that the fusion protein was well expressed without showing a significant difference among culturing solutions that culture the cells (position of 33 kDa in Loading sample (LS) lane). In addition, most of the proteins bound to the column were cleaved (33 kDa bands did not exist in all bound protein (BP) lanes).

Meanwhile, by changing the length of the linker, it could be confirmed that the proteins from which the tag was removed (positioned at 15 kDa in cleaved protein (CP) lane) were weakly present in 7 A.A. linker(GGSSRSS, SEQ ID NO: 5), and 18 A.A. linker (SSGGGGSGGGGGSSRSS, SEQ ID NO: 6). Meanwhile, the protein from which the tag was removed, with high purity and in a large amount was confirmed in 20 A.A. linker (SSGGGGSGGGGGSSRSSGS, SEQ ID NO: 7).

As a reason in which target protein yield of obtaining the protein including 20 A.A. linker is remarkably higher than that of the protein including 7 A.A. or 18 A.A. linker, firstly, in comparison in view of expression amount (LS lane), it could be confirmed that as compared to 7 A.A. linker, the fusion protein including 20 A.A. linker had higher over-expression degree; however, it could be confirmed that the fusion protein including 18 A.A. linker was over-expressed without significant difference between the protein including 18 A.A. linker and the protein including 20 A.A. linker. Meanwhile, as appreciated in each case by comparison between LS lane and FT lane, it was observed that the thick band of the over-expressed fusion protein (about 33 kDa) only including 20 A.A. linker disappeared in FT lane while passing through the column, which could be confirmed that the fusion protein including 20 A.A. linker had a remarkably high binding ratio to the column. It could be additionally confirmed that the protein portions (positioned at 20 kDa in Bound protein (BP) lane) removed while including remaining tag in the column were remarkably highly shown in the protein including 20 A.A. linker.

Accordingly, it was confirmed that the structure in which the 20 A.A. linker is inserted between the self-cleaving portion and Sortase is possible to remarkably increase yield of obtaining the target protein.

5-2: Whether or not Yield is Changed According to Addition of Linker

In order to confirm that yield is changed when the linker is present in C-terminal as well as N-terminal of the Sortase A domain, the fusion protein obtained by additionally inserting the linker between the Sortase A domain and His tag was used for comparison.

FIG. 13 shows comparison between (1) a case transformed with a vector expressing a fusion protein having a structure of target protein (VH)-LPETG-linker (20 A.A.)-Sortase A-His 6, and (2) a case transformed with a vector expressing a fusion protein having a structure of target protein (VH)-HA-LPETG-linker (20 A.A.)-Sortase A-linker (7 A.A.)-His 6.

Difference between (1) and (2) is the presence of the linker (7 A.A., GGSSRSS) behind the Sortase A. Expression and column binding degrees of two fusion proteins were confirmed by Coomassie blue staining.

As shown in FIG. 13, it could be confirmed that strong bands were shown at fusion protein portions (33 kDa) in both cases of (1) and (2). However, in (1), the proteins slightly bound to the column were confirmed (Bound proteins); and in (2) comparing with (1), proteins bound to the column were hardly confirmed. That is, the addition of the linker (7 A.A.) to C-terminal of Sortase A interferes the binding of the fusion protein to column.

5-3: Change of Linker

Binding ratio to column or yield was confirmed by substituting the linkers consisting of a plurality of glycine and serine and one arginine with various kinds of linkers capable of reducing interference among the domains.

First, the substitution was made with a helical linker. The helical linker having General Formula of A(EAAK)nA (n=2-5) was used, in particular, (H4)2 linker (LEA (EAAAK)4ALEA(EAAAK)4ALE, 50 A.A., SEQ ID NO: 1) (n=4) was used to express the fusion protein having structures of I and II of FIG. 2, and binding ratios of protein and column were confirmed.

As shown in FIG. 12, it could be confirmed that the corresponding fusion proteins were over-expressed, but rarely bound to the column. It was confirmed that the helical linker used in the corresponding fusion proteins could not have an effect of increasing the binding ratio.

Next, the substitution was made with a positively charged linker (CHL, TRARLSKELQAAQARLGADMEDVCGRL VQYRG, SEQ ID NO: 2) or a negatively charged linker (AHL, KEQQNAFYEILHLPNLNEE QRNGFIQSLKDDP-SQSANLLAEAKKL, SEQ ID NO: 3). Structures of the fusion proteins using the linkers were illustrated in I and II of FIG. 3. Binding ratio and yield of obtaining two fusion proteins were confirmed.

As shown in FIG. 14, the fusion protein including CHL (FIG. 14A) showed significantly weak expression, and was rarely bound to the column. Meanwhile, the fusion protein including AHL (FIG. 14B) showed some level of over-expression, and was bound to the column in a predetermined amount; however, cleaved protein (cleavage) was rarely shown. It was confirmed that the charged linker used in the corresponding fusion proteins could not have a sufficient effect of increasing the binding ratio or yield.

EXAMPLE 6

Optimum Conditions for Cleavage Reaction

In order for the Sortase A to recognize and cleave the cleavage sequence (LPXTG), it was known to require calcium and/or triglycine. In the present invention, yield of obtaining the cleavage protein was confirmed by including or not including calcium or triglycine and by changing concentration conditions in order to confirm optimum conditions of the cleavage reaction.

Specifically, yield of obtaining the cleavage protein by the cleavage-buffer in which one of calcium and triglycine having a concentration to be fixed as 5 mM and the remaining other one having a concentration of 0, 0.2, 1, or 5 mM are mixed is compared with that of a negative control group without including both of calcium and triglycine.

As shown in FIG. 11, in the negative control group, the cleavage protein was not observed at all (about 15 kDa), and in a case in which one of calcium and triglycine is included, the cleavage protein could be observed. Meanwhile, it could be confirmed that in a case of including 5 mM of triglycine and controlling concentration of calcium from 0 to 5 mM, there was little difference in an amount of cleavage protein to be obtained; meanwhile, in a case of including 5 mM of calcium and controlling concentration of triglycine from 0 to 5 mM, in particular, in a case of not including triglycine, the cleavage protein was obtained in a small amount (FIG. 11B). However, once triglycine is included, there was little difference in an amount of the cleavage protein to be obtained.

It means that triglycine included in the cleavage-buffer has an important role in cleavage function of Sortase, and the concentration difference does not have significant meaning.

EXAMPLE 7

Optimization for Preparing Therapeutic Antibody-drug Conjugate 7-1: Concentration Optimization In present example, optimum concentration condition of triglycine required for binding to effective drug was established. As the drug, biotin fused with triglycine was used. The reaction was made by mixing the drug with each concentration of 0, 10 nM, 100 nM, 500 nM, 1 µM, 10 µM, 100 µM, 500 µM, and 1 mM with reaction buffer (50 mM Tris buffer, pH8.0/150 mM NaCl/5 mM $CaCl_2$), and the target proteins-biotin conjugates were compared with negative control groups. For the negative control groups, three conditions (1: 50 mM Tris buffer, pH8.0/2:50 mM Tris buffer, pH8.0+500 µM triglycine-biotin/3: reaction buffer) were used. Total concentration of the target protein from the conjugation reaction of target protein-biotin was confirmed by Western blotting using a Myc tag bound to the target protein, and a conjugation reaction degree of the target protein and the biotin was confirmed by streptavidin.

As a result, in the negative control groups including three conditions as described above, the target protein-biotin conjugate (about 45 kDa) was not observed at all, and a saturated conjugation reaction could be observed in triglycine-biotin with a concentration of 500 µM and 1 mM, and a large amount of conjugation reactions could be observed in triglycine-biotin with a concentration of 100 µM; but had a lower reaction degree as compared to the triglycine-biotin conjugates with concentration of 500 µM and 1 mM (FIG. 16A).

7-2: Reaction Time Optimization

Optimum reaction time condition was analyzed by using the established concentration of triglycine-biotin as described in Example 7-1 above. The reaction was made by using the target proteins each with concentration to be fixed as 500 µM or 1 mM for reaction times of 0, 30 minutes, 1, 2, 3, 4, 6 hours, and 16 hours. Then, the target protein-biotin conjugates were compared with the negative control group.

As an analysis result obtained by Western blotting like Example 7-1, the target protein-biotin conjugate was not observed in the negative control group, a large amount of conjugation reactions was observed in triglycine-biotin with a concentration of 500 µM for 4 to 6 hours; and the best efficiency was shown in the conjugation reaction for hours. In addition, in triglycine-biotin with a concentration of 1 mM, it could be confirmed that excellent conjugation efficiency could be shown in all conjugation reactions for 4 to 6 hours and 16 hours (FIG. 16B).

When summarizing the above-described results, it could be appreciated that the fusion protein having a structure of target protein-LPETG-linker (20 A.A.)-Sortase-tag had significantly high yield due to excellent binding ability to column, and excellent Sortase A self-cleaving activity, and the therapeutic antibody-drug conjugate could be prepared by using the fusion protein.

INDUSTRIAL APPLICABILITY

The present invention relates to a self-cleaving fusion protein including a self-cleaving cassette consisting of a domain of Sortase A having cleaving function and a peptide including amino acid sequence represented by LPXTG which is a recognition sequence of the domain in Sortase A having cleaving function, which is significantly useful in that a purification process and a tag removing process of the target protein are capable of being completed by only one purification process rather than separate processes. In particular, the fusion protein may be widely used in various fields requiring proteins with high purity and in a large amount in that a binding ability of the fusion protein to the column, and a self-cleaving ability are increased, the target protein from which the tag is removed is capable of being obtained with high purity, and the purification process and the tag removing process of the target protein are capable of being completed by a cleavage-buffer to remarkably reduce time and efforts required for the purification, and loss of proteins to be obtained is reduced due to only one step, by positioning the target protein at the amino terminal. In particular, the fusion protein is useful for preparing a therapeutic antibody-drug conjugate.

The present invention has been described in detail based on particular features thereof, and it is obvious to those skilled in the art that these specific technologies are merely preferable embodiments and thus the scope of the present invention is not limited to the embodiments. Therefore, the substantial scope of the present invention will be defined by the accompanying claims and their equivalents.

SEQUENCE LISTING

<160> NUMBER OF SEQ ID NOS: 57

<210> SEQ ID NO 1

```
<211> LENGTH: 49
<212> TYPE: PRT
<213> ORGANISM: Artificial Sequence
<220> FEATURE:
<223> OTHER INFORMATION: Linker 50 a.a.

<400> SEQUENCE: 1

Leu Glu Ala Glu Ala Ala Ala Lys Glu Ala Ala Lys Glu Ala Ala
1               5                   10                  15

Ala Lys Glu Ala Ala Ala Lys Ala Leu Glu Glu Ala Ala Ala Lys
                20                  25                  30

Glu Ala Ala Ala Lys Glu Ala Ala Lys Glu Ala Ala Ala Lys Ala
            35                  40                  45

Leu

<210> SEQ ID NO 2
<211> LENGTH: 32
<212> TYPE: PRT
<213> ORGANISM: Artificial Sequence
<220> FEATURE:
<223> OTHER INFORMATION: CH Linker

<400> SEQUENCE: 2

Thr Arg Ala Arg Leu Ser Lys Glu Leu Gln Ala Ala Gln Ala Arg Leu
1               5                   10                  15

Gly Ala Asp Met Glu Asp Val Cys Gly Arg Leu Val Gln Tyr Arg Gly
                20                  25                  30

<210> SEQ ID NO 3
<211> LENGTH: 45
<212> TYPE: PRT
<213> ORGANISM: Artificial Sequence
<220> FEATURE:
<223> OTHER INFORMATION: AH Linker

<400> SEQUENCE: 3

Lys Glu Gln Gln Asn Ala Phe Tyr Glu Ile Leu His Leu Pro Asn Leu
1               5                   10                  15

Asn Glu Glu Gln Arg Asn Gly Phe Ile Gln Ser Leu Lys Asp Asp Pro
                20                  25                  30

Ser Gln Ser Ala Asn Leu Leu Ala Glu Ala Lys Lys Leu
            35                  40                  45

<210> SEQ ID NO 4
<211> LENGTH: 15
<212> TYPE: PRT
<213> ORGANISM: Artificial Sequence
<220> FEATURE:
<223> OTHER INFORMATION: Flexible Linker

<400> SEQUENCE: 4

Ser Ser Gly Gly Gly Gly Gly Gly Ser Ser Arg Ser Ser Gly Ser
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Linker 7 a.a.

<400> SEQUENCE: 5

Gly Gly Ser Ser Arg Ser Ser
1               5
```

<210> SEQ ID NO 6
<211> LENGTH: 18
<212> TYPE: PRT
<213> ORGANISM: Artificial Sequence
<220> FEATURE:
<223> OTHER INFORMATION: Linker 18 a.a.

<400> SEQUENCE: 6

Ser Ser Gly Gly Gly Gly Ser Gly Gly Gly Gly Gly Ser Ser Arg
1               5                   10                  15

Ser Ser

<210> SEQ ID NO 7
<211> LENGTH: 20
<212> TYPE: PRT
<213> ORGANISM: Artificial Sequence
<220> FEATURE:
<223> OTHER INFORMATION: Linker 20 a.a.

<400> SEQUENCE: 7

Ser Ser Gly Gly Gly Gly Ser Gly Gly Gly Gly Gly Ser Ser Arg
1               5                   10                  15

Ser Ser Gly Ser
            20

<210> SEQ ID NO 8
<211> LENGTH: 147
<212> TYPE: PRT
<213> ORGANISM: Artificial Sequence
<220> FEATURE:
<223> OTHER INFORMATION: S. aureus Sortase A 60-206

<400> SEQUENCE: 8

Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
            20                  25                  30

Ala Thr Pro Glu Gln Leu Asn Arg Gly Val Ser Phe Ala Glu Glu Asn
        35                  40                  45

Glu Ser Leu Asp Asp Gln Asn Ile Ser Ile Ala Gly His Thr Phe Ile
    50                  55                  60

Asp Arg Pro Asn Tyr Gln Phe Thr Asn Leu Lys Ala Ala Lys Lys Gly
65                  70                  75                  80

Ser Met Val Tyr Phe Lys Val Gly Asn Glu Thr Arg Lys Tyr Lys Met
                85                  90                  95

Thr Ser Ile Arg Asp Val Lys Pro Thr Asp Val Gly Val Leu Asp Glu
            100                 105                 110

Gln Lys Gly Lys Asp Lys Gln Leu Thr Leu Ile Thr Cys Asp Asp Tyr
        115                 120                 125

Asn Glu Lys Thr Gly Val Trp Glu Lys Arg Lys Ile Phe Val Ala Thr
    130                 135                 140

Glu Val Lys
145

<210> SEQ ID NO 9
<211> LENGTH: 39
<212> TYPE: PRT
<213> ORGANISM: Artificial Sequence
<220> FEATURE:
<223> OTHER INFORMATION: H1. winzipA1 coiled coil

<400> SEQUENCE: 9

Thr Val Ala Gln Leu Glu Glu Lys Val Lys Thr Leu Arg Ala Gln Asn
1               5                   10                  15

Tyr Glu Leu Lys Ser Arg Val Gln Arg Leu Arg Glu Gln Val Ala Gln
            20                  25                  30

Leu Ala Ser Glu Phe Glu Leu
        35

<210> SEQ ID NO 10
<211> LENGTH: 39
<212> TYPE: PRT
<213> ORGANISM: Artificial Sequence
<220> FEATURE:
<223> OTHER INFORMATION: H2.winzipA2 coiled coil linker

<400> SEQUENCE: 10

Thr Val Ala Gln Leu Arg Glu Arg Val Lys Thr Leu Arg Ala Gln Asn
1               5                   10                  15

Tyr Glu Leu Glu Ser Glu Val Gln Arg Leu Arg Glu Gln Val Ala Gln
            20                  25                  30

Leu Ala Ser Glu Phe Glu Leu
        35

<210> SEQ ID NO 11
<211> LENGTH: 39
<212> TYPE: PRT
<213> ORGANISM: Artificial Sequence
<220> FEATURE:
<223> OTHER INFORMATION: H3.Vel A1 coiled coil linker

<400> SEQUENCE: 11

Thr Val Ala Gln Leu Glu Glu Lys Val Lys Thr Leu Arg Ala Glu Asn
1               5                   10                  15

Tyr Glu Leu Lys Ser Glu Val Gln Arg Leu Glu Glu Gln Val Ala Gln
            20                  25                  30

Leu Ala Ser Glu Phe Glu Leu
        35

<210> SEQ ID NO 12
<211> LENGTH: 36
<212> TYPE: PRT
<213> ORGANISM: Artificial Sequence
<220> FEATURE:
<223> OTHER INFORMATION: H4.Max coiled coil linker

<400> SEQUENCE: 12

Thr Met Arg Arg Lys Asn Asp Thr His Gln Gln Asp Ile Asp Asp Leu
1               5                   10                  15

Lys Arg Gln Asn Ala Leu Leu Glu Gln Gln Val Arg Ala Leu Ala Ser
            20                  25                  30

Glu Phe Glu Leu
        35

<210> SEQ ID NO 13
<211> LENGTH: 52
<212> TYPE: PRT
<213> ORGANISM: Artificial Sequence
<220> FEATURE:
<223> OTHER INFORMATION: H5.EE1234L coiled coil linker

<400> SEQUENCE: 13

Thr Leu Glu Ile Glu Ala Ala Phe Leu Glu Gln Glu Asn Thr Ala Leu
1               5                   10                  15

Glu Thr Glu Val Ala Glu Leu Glu Gln Glu Val Gln Arg Leu Glu Asn
                20                  25                  30

Ile Val Ser Gln Tyr Glu Thr Arg Tyr Gly Pro Leu Gly Gly Ala Ser
            35                  40                  45

Glu Phe Glu Leu
    50

<210> SEQ ID NO 14
<211> LENGTH: 44
<212> TYPE: PRT
<213> ORGANISM: Artificial Sequence
<220> FEATURE:
<223> OTHER INFORMATION: H6.VSAL E5 coiled coil linker

<400> SEQUENCE: 14

Thr Glu Val Ser Ala Leu Lys Glu Lys Val Ser Ala Leu Glu Lys Glu
1               5                   10                  15

Val Ser Ala Leu Lys Glu Lys Val Ser Ala Leu Glu Lys Glu Val Ser
                20                  25                  30

Ala Leu Glu Lys Gly Gly Ala Ser Glu Phe Glu Leu
            35                  40

<210> SEQ ID NO 15
<211> LENGTH: 31
<212> TYPE: PRT
<213> ORGANISM: Artificial Sequence
<220> FEATURE:
<223> OTHER INFORMATION: H7.VSAL E3ox coiled coil linker

<400> SEQUENCE: 15

Thr Cys Gly Gly Glu Val Ser Ala Leu Glu Lys Glu Val Ser Ala Leu
1               5                   10                  15

Glu Lys Glu Val Ser Ala Leu Glu Lys Ala Ser Glu Phe Glu Leu
                20                  25                  30

<210> SEQ ID NO 16
<211> LENGTH: 28
<212> TYPE: PRT
<213> ORGANISM: Artificial Sequence
<220> FEATURE:
<223> OTHER INFORMATION: H8. IAALE3 coiled coil linker

<400> SEQUENCE: 16

Thr Glu Ile Ala Ala Leu Glu Lys Glu Ile Ala Ala Leu Glu Lys Glu
1               5                   10                  15

Ile Ala Ala Leu Glu Lys Ala Ser Glu Phe Glu Leu
                20                  25

<210> SEQ ID NO 17
<211> LENGTH: 374
<212> TYPE: PRT
<213> ORGANISM: Artificial Sequence
<220> FEATURE:
<223> OTHER INFORMATION: Flag-VH-linker- VSAL E3 ox coiled coil-
      HA-Flag-LPETG-linker 20-SrtA-His9

<400> SEQUENCE: 17

Asp Tyr Lys Asp Glu Val Gln Leu Val Glu Ser Gly Gly Gly Leu Val
1               5                   10                  15

Gln Pro Gly Gly Ser Leu Arg Leu Ser Cys Ala Ala Ser Gly Phe Asn
                20                  25                  30

Ile Lys Asp Thr Tyr Ile His Trp Val Arg Gln Ala Pro Gly Lys Gly
         35                  40                  45

Leu Glu Trp Val Ala Arg Ile Tyr Pro Thr Asn Gly Tyr Thr Arg Tyr
     50                  55                  60

Ala Asp Ser Val Lys Gly Arg Phe Thr Ile Ser Ala Asp Thr Ser Lys
 65                  70                  75                  80

Asn Thr Ala Tyr Leu Gln Met Asn Ser Leu Arg Ala Glu Asp Thr Ala
                 85                  90                  95

Val Tyr Tyr Cys Ser Arg Trp Gly Asp Gly Phe Tyr Ala Met Asp
             100                 105                 110

Tyr Trp Gly Gln Gly Thr Leu Val Thr Val Ser Ser Leu Glu Gly
             115                 120                 125

Thr Gly Gly Thr Ser Gly Ser Thr Ser Gly Thr Gly Gly Ser Ser Arg
130                 135                 140

Ser Ser Ser Thr Thr Cys Gly Gly Glu Val Ser Ala Leu Glu Lys Glu
145                 150                 155                 160

Val Ser Ala Leu Glu Lys Glu Val Ser Ala Leu Glu Lys Ala Ser Glu
                165                 170                 175

Phe Glu Leu Tyr Pro Tyr Asp Val Pro Asp Tyr Ala Lys Asp Tyr Lys
                180                 185                 190

Asp Leu Pro Glu Thr Gly Ser Ser Gly Gly Gly Gly Ser Gly Gly Gly
            195                 200                 205

Gly Gly Gly Ser Ser Arg Ser Ser Gly Ser Gln Ala Lys Pro Gln Ile
        210                 215                 220

Pro Lys Asp Lys Ser Lys Val Ala Gly Tyr Ile Glu Ile Pro Asp Ala
225                 230                 235                 240

Asp Ile Lys Glu Pro Val Tyr Pro Gly Pro Ala Thr Pro Glu Gln Leu
                245                 250                 255

Asn Arg Gly Val Ser Phe Ala Glu Glu Asn Glu Ser Leu Asp Asp Gln
            260                 265                 270

Asn Ile Ser Ile Ala Gly His Thr Phe Ile Asp Arg Pro Asn Tyr Gln
        275                 280                 285

Phe Thr Asn Leu Lys Ala Ala Lys Lys Gly Ser Met Val Tyr Phe Lys
    290                 295                 300

Val Gly Asn Glu Thr Arg Lys Tyr Lys Met Thr Ser Ile Arg Asp Val
305                 310                 315                 320

Lys Pro Thr Asp Val Gly Val Leu Asp Glu Gln Lys Gly Lys Asp Lys
                325                 330                 335

Gln Leu Thr Leu Ile Thr Cys Asp Asp Tyr Asn Glu Lys Thr Gly Val
            340                 345                 350

Trp Glu Lys Arg Lys Ile Phe Val Ala Thr Glu Val Lys His His
        355                 360                 365

His His His His His His
370

<210> SEQ ID NO 18
<211> LENGTH: 377
<212> TYPE: PRT
<213> ORGANISM: Artificial Sequence
<220> FEATURE:
<223> OTHER INFORMATION: VL-linker-VelB1 coiled coil- myc-LPETG-linker
      20- SrtA-His9

<400> SEQUENCE: 18

Asp Ile Gln Met Thr Gln Ser Pro Ser Ser Leu Ser Ala Ser Val Gly

```
  1               5                  10                 15
Asp Arg Val Thr Ile Thr Cys Arg Ala Ser Gln Asp Val Asn Thr Ala
             20                  25                 30

Val Ala Trp Tyr Gln Gln Lys Pro Gly Lys Ala Pro Lys Leu Leu Ile
             35                  40                 45

Tyr Ser Ala Ser Phe Leu Tyr Ser Gly Val Pro Ser Arg Phe Ser Gly
             50                  55                 60

Ser Arg Ser Gly Thr Asp Phe Thr Leu Thr Ile Ser Ser Leu Gln Pro
65                  70                  75                 80

Glu Asp Phe Ala Thr Tyr Tyr Cys Gln Gln His Tyr Thr Thr Pro Pro
                 85                  90                 95

Thr Phe Gly Gln Gly Thr Lys Val Glu Ile Lys Ala Leu Glu Gly Thr
                100                 105                110

Gly Ser Ser Thr Gly Ser Ser Thr Gly Pro Gly Gly Ser Ser Arg Ser
                115                 120                125

Ser Ser Thr Gly Pro Gly Gly Ser Ser Arg Ser Ser Ser Thr Ser Val
            130                 135                 140

Asp Glu Leu Gln Ala Glu Val Asp Gln Leu Glu Asp Glu Asn Tyr Ala
145                 150                 155                160

Leu Lys Thr Lys Val Ala Gln Leu Arg Lys Lys Val Glu Lys Leu Ala
                165                 170                175

Ser Glu Phe Glu Leu Gln Lys Leu Ile Ser Glu Gly Asp Leu Lys
                180                 185                190

Leu Pro Glu Thr Leu Pro Glu Thr Gly Ser Ser Gly Gly Gly Gly Ser
                195                 200                205

Gly Gly Gly Gly Gly Ser Ser Arg Ser Ser Gly Ser Gln Ala Lys
            210                 215                 220

Pro Gln Ile Pro Lys Asp Lys Ser Lys Val Ala Gly Tyr Ile Glu Ile
225                 230                 235                240

Pro Asp Ala Asp Ile Lys Glu Pro Val Tyr Pro Gly Pro Ala Thr Pro
                245                 250                255

Glu Gln Leu Asn Arg Gly Val Ser Phe Ala Glu Glu Asn Glu Ser Leu
                260                 265                270

Asp Asp Gln Asn Ile Ser Ile Ala Gly His Thr Phe Ile Asp Arg Pro
                275                 280                285

Asn Tyr Gln Phe Thr Asn Leu Lys Ala Ala Lys Lys Gly Ser Met Val
                290                 295                300

Tyr Phe Lys Val Gly Asn Glu Thr Arg Lys Tyr Lys Met Thr Ser Ile
305                 310                 315                320

Arg Asp Val Lys Pro Thr Asp Val Gly Val Leu Asp Glu Gln Lys Gly
                325                 330                335

Lys Asp Lys Gln Leu Thr Leu Ile Thr Cys Asp Asp Tyr Asn Glu Lys
                340                 345                350

Thr Gly Val Trp Glu Lys Arg Lys Ile Phe Val Ala Thr Glu Val Lys
                355                 360                365

His His His His His His His
                370                 375
```

<210> SEQ ID NO 19
<211> LENGTH: 50
<212> TYPE: DNA
<213> ORGANISM: Artificial Sequence
<220> FEATURE:
<223> OTHER INFORMATION: primer 1_sfi

<400> SEQUENCE: 19
ccgtggccca ggcggccgca agcagcggcc tgaacgacat cttcgaggcc        50

<210> SEQ ID NO 20
<211> LENGTH: 43
<212> TYPE: DNA
<213> ORGANISM: Artificial Sequence
<220> FEATURE:
<223> OTHER INFORMATION: primer 1

<400> SEQUENCE: 20
atgtcatatg gcaagcagcg gcctgaacga catcttcgag gcc               43

<210> SEQ ID NO 21
<211> LENGTH: 45
<212> TYPE: DNA
<213> ORGANISM: Artificial Sequence
<220> FEATURE:
<223> OTHER INFORMATION: primer 2

<400> SEQUENCE: 21
ctgcatttcg tgccactcga tcttctgggc ctcgaagatg tcgtt             45

<210> SEQ ID NO 22
<211> LENGTH: 39
<212> TYPE: DNA
<213> ORGANISM: Artificial Sequence
<220> FEATURE:
<223> OTHER INFORMATION: primer 3

<400> SEQUENCE: 22
atcgagtggc acgaaatgca ggctaagccg cagattccg                    39

<210> SEQ ID NO 23
<211> LENGTH: 39
<212> TYPE: DNA
<213> ORGANISM: Artificial Sequence
<220> FEATURE:
<223> OTHER INFORMATION: primer 4

<400> SEQUENCE: 23
gccggtctcg ggaagcttct tgacctcggt agcgacaaa                    39

<210> SEQ ID NO 24
<211> LENGTH: 43
<212> TYPE: DNA
<213> ORGANISM: Artificial Sequence
<220> FEATURE:
<223> OTHER INFORMATION: primer 5

<400> SEQUENCE: 24
cagtaagctt cccgagaccg gcgatatcca gatgactcag agc               43

<210> SEQ ID NO 25
<211> LENGTH: 36
<212> TYPE: DNA
<213> ORGANISM: Artificial Sequence
<220> FEATURE:
<223> OTHER INFORMATION: primer 6

<400> SEQUENCE: 25
actcgaaccc gccgtacgtt ttatctctac ctttgt                       36

<210> SEQ ID NO 26
<211> LENGTH: 52

```
<212> TYPE: DNA
<213> ORGANISM: Artificial Sequence
<220> FEATURE:
<223> OTHER INFORMATION: primer 7

<400> SEQUENCE: 26
taatggccgg cctggccgcg gccgcttaaa gatcttcttc actaattaac tt      52

<210> SEQ ID NO 27
<211> LENGTH: 31
<212> TYPE: DNA
<213> ORGANISM: Artificial Sequence
<220> FEATURE:
<223> OTHER INFORMATION: primer 8

<400> SEQUENCE: 27
atgtcatatg gacattcaga tgacacagag t                              31

<210> SEQ ID NO 28
<211> LENGTH: 46
<212> TYPE: DNA
<213> ORGANISM: Artificial Sequence
<220> FEATURE:
<223> OTHER INFORMATION: primer 9

<400> SEQUENCE: 28
ggaaccaccg ccggtctcgg gaagaagatc ttcttcacta attaac              46

<210> SEQ ID NO 29
<211> LENGTH: 74
<212> TYPE: DNA
<213> ORGANISM: Artificial Sequence
<220> FEATURE:
<223> OTHER INFORMATION: primer 10

<400> SEQUENCE: 29
ggaagatcta gaggaaccac ccccaccacc gcccgagcca ccgccaccgg atgagccggt    60
ctcgggaaga agat                                                     74

<210> SEQ ID NO 30
<211> LENGTH: 48
<212> TYPE: DNA
<213> ORGANISM: Artificial Sequence
<220> FEATURE:
<223> OTHER INFORMATION: primer 11

<400> SEQUENCE: 30
gagaccggcg gtggttcctc tagatcttcc caggctaagc cgcagatt            48

<210> SEQ ID NO 31
<211> LENGTH: 44
<212> TYPE: DNA
<213> ORGANISM: Artificial Sequence
<220> FEATURE:
<223> OTHER INFORMATION: primer 13

<400> SEQUENCE: 31
taatgcggcc gcttaatgat ggtgatggtg atgatgatga tggc                44

<210> SEQ ID NO 32
<211> LENGTH: 41
<212> TYPE: DNA
<213> ORGANISM: Artificial Sequence
<220> FEATURE:
<223> OTHER INFORMATION: primer 13
```

-continued

<400> SEQUENCE: 32
gtggttcctc tagatcttcc tcgaaggtcg cgggatatat t                41

<210> SEQ ID NO 33
<211> LENGTH: 49
<212> TYPE: DNA
<213> ORGANISM: Artificial Sequence
<220> FEATURE:
<223> OTHER INFORMATION: primer 14

<400> SEQUENCE: 33
taatggccgg cctggcctta atgatggtga tggtgatgat gatgatggc            49

<210> SEQ ID NO 34
<211> LENGTH: 42
<212> TYPE: DNA
<213> ORGANISM: Artificial Sequence
<220> FEATURE:
<223> OTHER INFORMATION: primer 15

<400> SEQUENCE: 34
ggttcctcta gatcttccgg aagccaggct aagccgcaga tt               42

<210> SEQ ID NO 35
<211> LENGTH: 56
<212> TYPE: DNA
<213> ORGANISM: Artificial Sequence
<220> FEATURE:
<223> OTHER INFORMATION: primer 16

<400> SEQUENCE: 35
atgatgatgg cgagagctac ggctgctgcc gcccttgacc tcggtagcga caaaga        56

<210> SEQ ID NO 36
<211> LENGTH: 57
<212> TYPE: DNA
<213> ORGANISM: Artificial Sequence
<220> FEATURE:
<223> OTHER INFORMATION: primer 17

<400> SEQUENCE: 36
taatgcggcc gcttaatgat ggtgatggtg atgatgatga tggcgagagc tacggct        57

<210> SEQ ID NO 37
<211> LENGTH: 100
<212> TYPE: DNA
<213> ORGANISM: Artificial Sequence
<220> FEATURE:
<223> OTHER INFORMATION: primer 18

<400> SEQUENCE: 37
acgacgacga cggcgctcca gtgccttagc agcggcttcc ttagcagcag cctccttagc      60
agctgcttct ttcgctgcgg cttccgcttc caacgctttc                100

<210> SEQ ID NO 38
<211> LENGTH: 52
<212> TYPE: DNA
<213> ORGANISM: Artificial Sequence
<220> FEATURE:
<223> OTHER INFORMATION: primer 19

<400> SEQUENCE: 38
taatgcggcc gcttaacggc gacgacggcg acgacgacga cggcgctcca gt          52

<210> SEQ ID NO 39
<211> LENGTH: 37
<212> TYPE: DNA
<213> ORGANISM: Artificial Sequence
<220> FEATURE:
<223> OTHER INFORMATION: primer 20

<400> SEQUENCE: 39
gtgcccgcgt cttgacctcg gtagcgacaa agatctt        37

<210> SEQ ID NO 40
<211> LENGTH: 49
<212> TYPE: DNA
<213> ORGANISM: Artificial Sequence
<220> FEATURE:
<223> OTHER INFORMATION: primer 21

<400> SEQUENCE: 40
gctgtccaag gagctgcagg cggcgcaggc ccggctgggc gcggacatg        49

<210> SEQ ID NO 41
<211> LENGTH: 52
<212> TYPE: DNA
<213> ORGANISM: Artificial Sequence
<220> FEATURE:
<223> OTHER INFORMATION: primer 22

<400> SEQUENCE: 41
gcggtactgc accaggcggc cgcacacgtc ctccatgtcc gcgcccagcc gg        52

<210> SEQ ID NO 42
<211> LENGTH: 39
<212> TYPE: DNA
<213> ORGANISM: Artificial Sequence
<220> FEATURE:
<223> OTHER INFORMATION: primer 23

<400> SEQUENCE: 42
gaggtcaaga cgcgggcacg gctgtccaag gagctgcag        39

<210> SEQ ID NO 43
<211> LENGTH: 53
<212> TYPE: DNA
<213> ORGANISM: Artificial Sequence
<220> FEATURE:
<223> OTHER INFORMATION: primer 24

<400> SEQUENCE: 43
taatgcggcc gcttaatgat gctgatggtg atggccgcgg tactgcacca ggc        53

<210> SEQ ID NO 44
<211> LENGTH: 36
<212> TYPE: DNA
<213> ORGANISM: Artificial Sequence
<220> FEATURE:
<223> OTHER INFORMATION: primer 25

<400> SEQUENCE: 44
cggatcaccc ttgacctcgg tagcgacaaa gatctt        36

<210> SEQ ID NO 45
<211> LENGTH: 36
<212> TYPE: DNA
<213> ORGANISM: Artificial Sequence
<220> FEATURE:
<223> OTHER INFORMATION: primer 26

<400> SEQUENCE: 45
gaggtcaagg gtgatccgaa agctgacaac aaattc    36

<210> SEQ ID NO 46
<211> LENGTH: 41
<212> TYPE: DNA
<213> ORGANISM: Artificial Sequence
<220> FEATURE:
<223> OTHER INFORMATION: primer 27

<400> SEQUENCE: 46
gtgatgatga tgatggtgag cttttggtgc ttgtgcatca t    41

<210> SEQ ID NO 47
<211> LENGTH: 54
<212> TYPE: DNA
<213> ORGANISM: Artificial Sequence
<220> FEATURE:
<223> OTHER INFORMATION: primer 28

<400> SEQUENCE: 47
taatgcggcc gcttaatgat ggtgatggtg atgatgatga tggtgagctt ttgg    54

<210> SEQ ID NO 48
<211> LENGTH: 39
<212> TYPE: PRT
<213> ORGANISM: Artificial Sequence
<220> FEATURE:
<223> OTHER INFORMATION: L1.wizipB1 coiled coil linker

<400> SEQUENCE: 48

Ser Val Asp Glu Leu Gln Ala Glu Val Asp Gln Leu Gln Asp Glu Asn
1               5                   10                  15

Tyr Ala Leu Lys Thr Lys Val Ala Gln Leu Arg Lys Lys Val Glu Lys
            20                  25                  30

Leu Ala Ser Glu Phe Glu Leu
        35

<210> SEQ ID NO 49
<211> LENGTH: 50
<212> TYPE: PRT
<213> ORGANISM: Artificial Sequence
<220> FEATURE:
<223> OTHER INFORMATION: L2.winzipB2 coiled coil linker

<400> SEQUENCE: 49

Gly Pro Gly Gly Ser Ser Arg Ser Ser Thr Ser Val Asp Glu Leu
1               5                   10                  15

Lys Ala Glu Val Asp Gln Leu Gln Asp Gln Asn Tyr Ala Leu Arg Thr
            20                  25                  30

Lys Val Ala Gln Leu Arg Lys Glu Val Glu Lys Leu Ser Glu Glu Phe
        35                  40                  45

Glu Leu
    50

<210> SEQ ID NO 50
<211> LENGTH: 50
<212> TYPE: PRT
<213> ORGANISM: Artificial Sequence
<220> FEATURE:
<223> OTHER INFORMATION: L3. Vel B1 coiled coil linker

<400> SEQUENCE: 50

```
Gly Pro Gly Gly Ser Ser Arg Ser Ser Thr Ser Val Asp Glu Leu
1               5                   10                  15

Gln Ala Glu Val Asp Gln Leu Glu Asp Glu Asn Tyr Ala Leu Lys Thr
            20                  25                  30

Lys Val Ala Gln Leu Arg Lys Lys Val Glu Lys Leu Ala Ser Glu Phe
        35                  40                  45

Glu Leu
    50
```

<210> SEQ ID NO 51
<211> LENGTH: 47
<212> TYPE: PRT
<213> ORGANISM: Artificial Sequence
<220> FEATURE:
<223> OTHER INFORMATION: L4. myc coiled coil linker

<400> SEQUENCE: 51

```
Gly Pro Gly Gly Ser Ser Arg Ser Ser Thr Ser Val Gln Ala Glu
1               5                   10                  15

Glu Gln Lys Leu Ile Ser Glu Glu Asp Leu Leu Arg Lys Arg Arg Glu
            20                  25                  30

Gln Leu Lys His Lys Leu Glu Gln Leu Ala Ser Glu Phe Glu Leu
        35                  40                  45
```

<210> SEQ ID NO 52
<211> LENGTH: 64
<212> TYPE: PRT
<213> ORGANISM: Artificial Sequence
<220> FEATURE:
<223> OTHER INFORMATION: L5. RR1234L coiled coil

<400> SEQUENCE: 52

```
Gly Pro Gly Gly Ser Ser Arg Ser Ser Thr Ser Lys Gly Gly Gly
1               5                   10                  15

Leu Glu Ile Arg Ala Ala Phe Leu Arg Arg Arg Asn Thr Ala Leu Arg
            20                  25                  30

Thr Arg Val Ala Glu Leu Arg Gln Arg Val Gln Arg Leu Arg Asn Ile
        35                  40                  45

Val Ser Gln Tyr Glu Thr Arg Tyr Gly Pro Ala Ser Phe Glu Glu Leu
    50                  55                  60
```

<210> SEQ ID NO 53
<211> LENGTH: 52
<212> TYPE: PRT
<213> ORGANISM: Artificial Sequence
<220> FEATURE:
<223> OTHER INFORMATION: L6. VSAL K5 coiled coil linker

<400> SEQUENCE: 53

```
Gly Pro Gly Gly Ser Ser Arg Ser Ser Thr Lys Val Ser Ala Leu
1               5                   10                  15

Lys Glu Lys Val Ser Ala Leu Lys Glu Lys Val Ser Ala Leu Lys Glu
            20                  25                  30

Lys Val Ser Ala Leu Lys Glu Lys Val Ser Ala Leu Lys Glu Gly Gly
        35                  40                  45

Glu Phe Glu Leu
    50
```

<210> SEQ ID NO 54
<211> LENGTH: 41
<212> TYPE: PRT

<213> ORGANISM: Artificial Sequence
<220> FEATURE:
<223> OTHER INFORMATION: L7. VSAL k3ox coiled coil linker

<400> SEQUENCE: 54

Gly Pro Gly Gly Ser Ser Arg Ser Ser Thr Cys Gly Gly Lys Val
1               5                   10                  15

Ser Ala Leu Lys Glu Lys Val Ser Ala Leu Lys Glu Lys Val Ser Ala
            20                  25                  30

Leu Lys Glu Gly Gly Glu Phe Glu Leu
        35                  40

<210> SEQ ID NO 55
<211> LENGTH: 39
<212> TYPE: PRT
<213> ORGANISM: Artificial Sequence
<220> FEATURE:
<223> OTHER INFORMATION: L8.IAAL K3 coiled coil linker

<400> SEQUENCE: 55

Gly Pro Gly Gly Ser Ser Arg Ser Ser Thr Ser Lys Ile Ala Ala
1               5                   10                  15

Leu Lys Glu Lys Ile Ala Ala Leu Lys Glu Lys Ile Ala Ala Leu Lys
            20                  25                  30

Glu Ala Ser Glu Phe Glu Leu
        35

<210> SEQ ID NO 56
<211> LENGTH: 1128
<212> TYPE: DNA
<213> ORGANISM: Artificial Sequence
<220> FEATURE:
<223> OTHER INFORMATION: Flag-VH-linker- VSAL E3 ox coiled coil-
      HA-Flag-LPETG-linker 20-SrtA-His9

<400> SEQUENCE: 56

| | | |
|---|---|---|
| gattataaag atgaagtgca gcttgttgaa agtggcggcg gtctggtaca gcctggaggt | 60 |
| agtttacgtc tgtcatgcgc ggcatctgga ttcaatataa agatacata tattcactgg | 120 |
| gtccgccagg caccggggaa aggattagaa tgggtagctc gtatttaccc aacgaatggt | 180 |
| tatactcgct atgccgactc cgtgaagggc agatttacca tctcggcgga tacgtcaaaa | 240 |
| aacaccgcct atttgcagat gaacagcctg cgggctgaag atactgcagt ttattactgt | 300 |
| tctcgttggg gtggtgacgg gttttacgcc atggattatt ggggtcaagg taccttagtt | 360 |
| acagtgtcta gtagcctcga gggtaccggc ggtaccagcg ttctaccag cggcaccggc | 420 |
| ggcagctctc gtagcagctc taccacctgc ggcggtgaag tgagcgcgct ggaaaaagaa | 480 |
| gttagcgcgc tggaaaagga agtgagcgcc ctggaaaaag cgagcgaatt cgagctctac | 540 |
| ccatacgatg ttccagatta cgctaaggat tataaagatg aacttcccga gaccggctca | 600 |
| tccggtggcg gtggctcggg cggtggtggg ggtggttcct ctagatcttc cggaagccag | 660 |
| gctaagccgc agattccgaa ggataagtcg aaggtcgcgg gatatattga aattcccgac | 720 |
| gccgatataa aggaaccagt gtatcctggg ccagccactc ctgaacagtt aaatcggggg | 780 |
| gtgagctttg cagaagaaaa tgaaagcctg gacgaccaga catttcaat gcgggccat | 840 |
| acgttcatcg accgtccgaa ctaccagttc accaatctga aggcggccaa gaagggttcc | 900 |
| atggtttatt ttaaagtggg caacgaaaca cgcaagtata aaatgacatc tatcagagat | 960 |
| gttaaaccga cagatgtagg agttttagat gaacaaaagg gtaaggataa gcaactcacg | 1020 |

```
-continued ctgataactt gcgatgacta caatgagaag acgggcgttt gggaaaagcg taagatcttt    1080
gtcgctaccg aggtcaagca ccatcatcat catcaccatc accatcat                 1128

<210> SEQ ID NO 57
<211> LENGTH: 1086
<212> TYPE: DNA
<213> ORGANISM: Artificial Sequence
<220> FEATURE:
<223> OTHER INFORMATION: VL-linker-VelB1 coiled coil- myc-LPETG-linker
      20- SrtA-His9

<400> SEQUENCE: 57
gatatccaga tgactcagag cccgagtagc ttgtccgcat cggtgggtga ccgtgttaca     60
atcacgtgtc gtgcgtctca ggatgttaac actgccgtgg cttggtatca gcaaaaaccg    120
ggcaaagctc ccaaactgct gatttactcg gcgtcattct tatattctgg cgtcccatct    180
cgttttagcg gaagtcgctc cgggaccgat tttacactca ccattagctc actgcaacct    240
gaagactttg caacctatta ttgccagcaa cactatacga ccccgccaac ctttggtcag    300
ggtacaaagg tagagataaa agcgctcgag ggtaccggca gcagcaccgg ttctagcacc    360
ggcccgggcg gcagctctcg tagcagctct accagcgtgg atgaactgca ggcggaagtg    420
gatcagctgg aagatgaaaa ctacgcgctg aaaaccaaag tggcccagct gcgtaaaaag    480
gtggaaaaac tgagcgaaga attcgagctc gagcaaaagt taattagtga agaagatctt    540
aagcttcccg agaccggctc atccggtggc ggtggctcgg gcggtggtgg ggtggttcc     600 tctagatctt ccggaagcca ggctaagccg cagattccga aggataagtc gaaggtcgcg    660
ggatatattg aaattcccga cgccgatata aaggaaccag tgtatcctgg gccagccact    720
cctgaacagt aaatcgggg ggtgagcttt gcagaagaaa atgaaagcct ggacgaccag    780
aacatttcaa ttgcgggcca tacgttcatc gaccgtccga actaccagtt caccaatctg    840
aaggcggcca agaagggttc catggtttat tttaaagtgg gcaacgaaac acgcaagtat    900
aaaatgacat ctatcagaga tgttaaaccg acagatgtag gagttttaga tgaacaaaag    960
ggtaaggata gcaactcac gctgataact tgcgatgact acaatgagaa gacgggcgtt    1020
tgggaaaagc gtaagatctt tgtcgctacc gaggtcaagc atcatcatca tcaccatcac    1080
catcat                                                               1086
```

The invention claimed is:

1. A self-cleaving fusion protein comprising:
   (i) a target protein;
   (ii) a peptide represented by Formula I below;
   (iii) a domain of Sortase A having cleaving function; and
   (iv) a tag, wherein (i) to (iv) are sequentially positioned from amino terminus to carboxyl terminus of the fusion protein, L-P-X-T-G (SEQ ID NO:58),  [Formula I]

wherein L represents Leucine, P represents Proline, X represents an any amino acid, T represents Threonine, G represents Glycine, and
   a peptide linker between (ii) a peptide represented by Formula I and (iii) a domain of Sortase A having cleaving function, wherein the linker is represented by Sc(SG4)1(GGSSRSS)GdSe (SEQ ID NO:4), in which S represents Serine, G represents Glycine, R represents Arginine, c represents 0 to 5, d represents 0 to 5, e represents 0 to 5, and 1 represents 0 to 10.

2. The self-cleaving fusion protein according to claim 1, wherein X in Formula I is glutamic acid.

3. The self-cleaving fusion protein according to claim 1, wherein the peptide linker consists of 19 to 40 amino acids.

4. The self-cleaving fusion protein according to claim 1, wherein the peptide linker consists of 19 to 25 amino acids.

5. The self-cleaving fusion protein according to claim 1, wherein the peptide linker comprises SEQ ID NO: 7.

6. The self-cleaving fusion protein according to claim 1, wherein the Sortase A is derived from *Staphylococcus aureus* (*S. aureus*).

7. The self-cleaving fusion protein according to claim 1, wherein the domain of Sortase A having cleaving function comprises SEQ ID NO: 8.

8. The self-cleaving fusion protein according to claim 1, wherein the tag is selected from the group consisting of a poly-histidine tag, a glutathione-S-transferase tag, a Hemagglutinin tag, a FLAG tag, a Myc tag, a maltose binding protein tag, a chitin binding protein tag, and a fluorescent tag.

9. The self-cleaving fusion protein according to claim 8, wherein the tag is a poly-histidine tag.

10. The self-cleaving fusion protein according to claim 9, wherein the poly-histidine tag comprises sequential 6 to 12 histidines.

11. The self-cleaving fusion protein according to claim 1, wherein the target protein is selected from the group consisting of polymer proteins, glycoproteins, cytokines, growth factor, blood preparations, vaccines, hormones, enzymes and antibodies.

12. The self-cleaving fusion protein according to claim 1, wherein the target protein is a portion or whole of a light chain or a heavy chain of an antibody.

13. The self-cleaving fusion protein according to claim 12, wherein the target protein is a light chain variable region (VL) or a heavy chain variable region (VH) of an antibody.

14. The self-cleaving fusion protein according to claim 1, wherein the fusion protein comprises an amino acid sequence represented by SEQ ID NO: 17 or 18.

15. A nucleic acid encoding the self-cleaving fusion protein according to any one of claims 1 to 14.

16. An expression vector comprising the nucleic acid of claim 15.

17. A host cell transformed with the expression vector of claim 16.

18. The host cell according to claim 17, wherein the host cell is prokaryotic or eukaryotic cell.

19. The host cell according to claim 18, wherein the host cell is *Escherichia coli*.

20. The host cell according to claim 19, wherein *Escherichia coli* is Origami2(DE3) or BL21(DE3).

21. A method for purifying a target protein comprising: (1) culturing cells of claim 17 to obtain cell lysates; and (2) purifying the target protein from the cell lysates.

22. The method for purifying a target protein of claim 21, wherein (2) comprises:
    (a) injecting the cell lysates into a column bound to a tag in a fusion protein;
    (b) washing the column;
    (c) equilibrating the column by using a cleavage buffer including at least one selected from the group consisting of calcium and triglycine to perform a cleaving reaction; and
    (d) obtaining the cleavage-buffer from the column to obtain the target protein from which the tag is removed.

23. The method for purifying a target protein of claim 22, wherein the cleavage-buffer in the step (c) comprises at least triglycine.

24. The method for purifying a target protein of claim 22, wherein the cleavage-buffer in the step (c) comprises 0.1 to 10 mM of calcium and 0.1 to 10 mM of triglycine.

25. The method for purifying a target protein of claim 24, wherein the cleavage-buffer in the step (c) comprises 0.2 to 5 mM of calcium and 0.2 to 5 mM of triglycine.

26. A method of preparing a therapeutic antibody-drug conjugate comprising:
    (1) reacting the self-cleaving fusion protein of claim 12 with triglycine-drug (GGG-drug) in a cleavage buffer including calcium to conjugate the triglycine-drug (GGG-drug) to the target protein;
    (2) obtaining the cleavage buffer and recovering a conjugate of the target protein in which the tag is removed with the triglycine-drug.

27. The method of preparing a therapeutic antibody-drug conjugate of claim 26, wherein the cleavage-buffer in the step (1) comprises 0.1 to 10 mM of calcium.

28. The method of preparing a therapeutic antibody-drug conjugate of claim 26, wherein the step (1) comprises 500 μM to 1 mM of triglycine-drug (GGG-drug).

29. The method of preparing a therapeutic antibody-drug conjugate of claim 26, wherein the step (1) comprises reacting the self-cleaving fusion protein with triglycine-drug (GGG-drug) for 3 to 16 hours.

30. The method of preparing a therapeutic antibody-drug conjugate of claim 26, wherein the target protein is an antibody against a tumor surface antigen.

* * * * *

UNITED STATES PATENT AND TRADEMARK OFFICE
CERTIFICATE OF CORRECTION

PATENT NO. : 10,077,299 B2
APPLICATION NO. : 14/785881
DATED : September 18, 2018
INVENTOR(S) : Song et al.

Page 1 of 2

It is certified that error appears in the above-identified patent and that said Letters Patent is hereby corrected as shown below:

In the Specification

Column 12, Line 46, replace:
5'-IAA
With:
5'-TAA

Column 19, In the Sequence Listing, SEQ ID NO 4, replace:
<210> SEQ ID NO 4
<211> LENGTH: 15
<212> TYPE: PRT
<213> ORGANISM: Artificial Sequence
<220> FEATURE:
<223> OTHER INFORMATION: Flexible Linker

<400> SEQUENCE: 4

Ser Ser Gly Gly Gly Gly Gly Gly Ser Ser Arg Ser Ser Gly Ser
1               5                   10                  15

With:
<210> SEQ ID NO 4
<211> LENGTH: 15
<212> TYPE: PRT
<213> ORGANISM: Artificial Sequence
<220> FEATURE:
<223> OTHER INFORMATION: Flexible Linker
<220> FEATURE:
<221> NAME/KEY: repeat Signed and Sealed this
Fourteenth Day of May, 2019

Andrei Iancu
*Director of the United States Patent and Trademark Office*

CERTIFICATE OF CORRECTION (continued)
U.S. Pat. No. 10,077,299 B2

```
<222> LOCATION: (2) .. (6)
<223> OTHER INFORMATION: 'SGGGG' can be repeated from 0 to 10 times
<220> FEATURE:
<221> NAME/KEY: repeat
<222> LOCATION: (1)
<223> OTHER INFORMATION: 'S' can be repeated from 0 to 5 times
<220> FEATURE:
<221> NAME/KEY: repeat
<222> LOCATION: (14)
<223> OTHER INFORMATION: 'G' can be repeated from 0 to 5 times
<220> FEATURE:
<221> NAME/KEY: repeat
<222> LOCATION: (15)
<223> OTHER INFORMATION: 'S' can be repeated from 0 to 5 times

<400> SEQUENCE: 4

Ser Ser Gly Gly Gly Gly Gly Gly Ser Ser Arg Ser Ser Gly Ser
1               5                   10                  15
```

In the Sequence Listing, please add SEQ ID NO 58 and SEQ ID NO 59, as follows:

```
<210> SEQ ID NO 58
<211> LENGTH: 5
<212> TYPE: PRT
<213> ORGANISM: Artificial Sequence
<220> FEATURE:
<223> OTHER INFORMATION: general Sortase A recognition sequence
<220> FEATURE:
<221> NAME/KEY: misc_feature
<222> LOCATION: (3) .. (3)
<223> OTHER INFORMATION: Xaa can be any amino acid

<400> SEQUENCE: 58

Leu Pro Xaa Thr Gly
1               5

<210> SEQ ID NO 59
<211> LENGTH: 5
<212> TYPE: PRT
<213> ORGANISM: Artificial Sequence
<220> FEATURE:
<223> OTHER INFORMATION: specific Sortase A recognition sequence

<400> SEQUENCE: 59

Leu Pro Glu Thr Gly
1               5
```